United States Patent
Huang et al.

(10) Patent No.: US 10,994,009 B2
(45) Date of Patent: May 4, 2021

(54) COMPOSITIONS AND METHODS OF TREATING SARCOMA LUNG METASTASIS

(71) Applicant: CASE WESTERN RESERVE UNIVERSITY, Cleveland, OH (US)

(72) Inventors: Alex Yee-Chen Huang, Solon, OH (US); Jay T. Myers, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/018,741

(22) Filed: Jun. 26, 2018

(65) Prior Publication Data
US 2018/0369372 A1    Dec. 27, 2018

Related U.S. Application Data

(60) Provisional application No. 62/525,080, filed on Jun. 26, 2017.

(51) Int. Cl.
| | |
|---|---|
| *A61K 39/00* | (2006.01) |
| *A61K 39/395* | (2006.01) |
| *A61P 35/00* | (2006.01) |
| *A61K 45/06* | (2006.01) |
| *A61K 38/17* | (2006.01) |
| *A61K 31/663* | (2006.01) |
| *C07K 16/28* | (2006.01) |
| *A61K 41/17* | (2020.01) |

(52) U.S. Cl.
CPC ........ *A61K 39/3955* (2013.01); *A61K 31/663* (2013.01); *A61K 38/1774* (2013.01); *A61K 41/17* (2020.01); *A61K 45/06* (2013.01); *A61P 35/00* (2018.01); *C07K 16/2842* (2013.01); *A61K 2039/505* (2013.01); *A61K 2039/543* (2013.01); *A61K 2039/544* (2013.01); *A61K 2039/585* (2013.01); *A61K 2300/00* (2013.01); *C07K 2317/76* (2013.01)

(58) Field of Classification Search
None
See application file for complete search history.

(56) References Cited

U.S. PATENT DOCUMENTS

2012/0171159 A1* 7/2012 Fensterle ............... A61K 35/74
424/93.2

OTHER PUBLICATIONS

Sousa S., Määttä J.A. Macrophages and pathophysiology of bone cancers. In: Heymann D., editor. Bone Cancer. Second ed. Academic Press; San Diego: 2015. pp. 91-101 (Year: 2015).*

Sousa S., Määttä J.A. The role of tumour-associated macrophages in bone metastasis. J Bone Oncol. Sep. 2016; 5(3): 135-138. Online Apr. 8, 2016. (Year: 2016).*
Le Noci et al. Reprogramming the lung microenvironment by inhaled immunotherapy fosters immune destruction of tumor. Oncoimmunology, Published online Sep. 20, 2016, vol. 5, No. 11, e1234571) (Year: 2016).*
Le Noci et al. Poly(I:C) and CpG-ODN combined aerosolization to treat lung metastases and counter the immunosuppressive microenvironment. Oncolmmunology 2015; 4(10):e1040214; (Year: 2015).*
Buddingh et al. Tumor-Infiltrating Macrophages Are Associated with Metastasis Suppression in High-Grade Osteosarcoma: A Rationale for Treatment with Macrophage Activating Agents. Clin Cancer Res; 17(8); 2110-9. (Year: 2011).*
Chen, Q and Massague, J., Molecular Pathways:VCAM-1 as a potential therapeutic target in metastasis. Clin Cancer Res. Oct. 15, 2012;18(20):5520-5. (Year: 2012).*
Decker et al. Adhesion of osteosarcoma cells to the 70-kDa core region of thrombospondin-1 is mediated by the a4β1 integrin. Biochemical and Biophysical Research Communications 293 (2002) 86-92 (Year: 2002).*
Lu et al. VCAM-1 Promotes Osteolytic Expansion of Indolent Bone Micrometastasis of Breast Cancer by Engaging a4b1-Positive Osteoclast Progenitors. Cancer Cell 20, 701-714, Dec. 13, 2011. (Year: 2011).*
Marco et al. α4 Integrin Increases Anoikis of Human Osteosarcoma Cells. J. Cell. Biochem. 88: 1038-1047, 2003 (Year: 2003).*
Chen et al. Macrophage binding to receptor VCAM-1 transmits survival signals in breast cancer cells that invade the lungs. Cancer Cell. Oct. 18, 2011; 20(4): 538-549. (Year: 2011).*
Lu et al. VCAM-1 Promotes Osteolytic Expansion of Indolent Bone Micrometastasis of Breast Cancer by Engaging rx4J31-Positive Osteoclast Progenitors. Cancer Cell 20, 701-714, Dec. 13, 2011. (Year: 2011).*
Taichman et al. Tumor cell surface a4β1 integrin mediates adhesion to vascular endothelium: demonstration of an interaction with the N-terminal domains of INCAM-1 1 O/VCAM-1. Cell Regulation, vol. 2, 347-355, May 1991. (Year: 1991).*
Assche, et al., "Progressive Multifocal Leukoencephalopathy after Natalizumab Therapy for Crohn's Disease", N Engl J Med, 362-368, Jul. 28, 2005.
Wu, et al., "Distinct FAK-Src activation events promote a5β1 and a4β1 integrin-stimulated neuroblastoma cell motility", Oncogene. Feb. 28, 2008; 27(10): 1439-1448.
Lloyd M. Stoolman, "Adhesion Molecules Controlling Lymphocyte Migration", Cell, vol. 56, 907-910, Mar. 24, 1989.
Caliera, et al., "Adhesion molecules in human pancreatic cancer", J Surg Oncol. Feb. 2002;79(2):93-100.
Slack-Davis et sl., "Vascular Cell Adhesion Molecule-1 Is a Regulator of Ovarian Cancer Peritoneal Metastasis", Cancer Res 2009; 69: (4). Feb. 15, 2009.
Silva, et al., "Soluble VCAM-1 and E-selectin in breast cancer: relationship with staging and with the detection of circulating cancer cells", NEOPLASMA, 53, 6, 2006.

(Continued)

*Primary Examiner* — Maher M Haddad

(74) *Attorney, Agent, or Firm* — Tarolli, Sundheim, Covell & Tummino LLP

(57) ABSTRACT

A method of treating pulmonary metastasis of osteosarcoma cells (pOSs) in a subject in need thereof includes administering to the subject a therapeutically effective amount of an agent that interferes with VCAM-1/α4β1 signaling between pOSs expressing VCAM-1 and pulmonary macrophages (MACs) expressing α4β1.

4 Claims, 20 Drawing Sheets

Specification includes a Sequence Listing.

(56) References Cited

OTHER PUBLICATIONS

Simmons, et al., "Vascular Cell Adhesion Molecule-1 Expressed by Bone Marrow Stromal Cells Mediates the Binding of Hematopoietic Progenitor Cells", Blood, vol. 80, No. 2 Jul. 15, 1992: pp. 388-395.

Shukla, et al., "Multiple Administrations of Viral Nanoparticles Alter in Vivo Behavior—Insights from Intravital Microscopy", ACS Biomater Sci Eng. May 9, 2016; 2(5): 829-837.

Schadenorf, et al., "Tumour progression and metastatic behaviour in vivo correlates with integrin expression on melanocytic tumours", J Pathol. Aug. 1993;170(4):429-34.

Scrimieri, et al., "Murine leukemia virus envelope gp70 is a shared biomarker for the high-sensitivity quantification of murine tumor burden", OncoImmunology 2:11, e26889; Nov. 2013.

Redondo-Munoz, et al., "MMP-9 in B-cell chronic lymphocytic leukemia is up-regulated by a4B1 integrin or CXCR4 engagement via distinct signaling pathways, localizes to podosomes, and is involved in cell invasion and migration", Blood, Nov. 1, 2006, vol. 108, No. 9.

Salomon, et al., "Vascular Cell Adhesion Molecule-1 Is Expressed by Cortical Thymic Epithelial Cells and Mediates Thymocyte Adhesion. Implications for the Function of a4b1 (VLA4) Integrin in T-Cell Development", Blood, vol. 89, No. 7 Apr. 1, 1997: pp. 2461-2471.

Zourab, et al., "Role of integrins in invasion of endometrial cancer cell lines", Gynecol Oncol. Jan. 2002;84(1):12-20.

Qian, et al., "Baseline levels and decrease in serum soluble intercellular adhesion molecule-1 during chemotherapy predict objective response and survival in patients who have advanced non-small-cell lung cancer", Clin Lung Cancer. Mar. 2011;12(2):131-7.

Paavonen, et al., "In vivo evidence of the role of alpha 4 beta 1-VCAM-1 interaction in sarcoma, but not in carcinoma extravasation", Int J Cancer. Jul. 15, 1994;58(2):298-302.

Nasu, et al., "Increased serum concentrations of soluble vascular cell adhesion molecule-1 in uterine cervical cancer", Gynecol Obstet Invest. 1998;45(4):269-71.

Pezzetti, et al., "A comparison between genetic portraits of normal osteoblasts and osteosarcoma cell lines", vol. 1, 52-59, 2009.

Okugawa, et al., "Serum level of soluble vascular cell adhesion molecule 1 is a valuable prognostic marker in colorectal carcinoma", Dis Colon Rectum. Jul. 2009;52(7):1330-6.

Nahrendorf, et al., "Noninvasive Vascular Cell Adhesion Molecule-1 Imaging Identifies Inflammatory Activation of Cells in Atherosclerosis", Oct. 3, 2006.

Morrow, et al., "mTOR Inhibition Mitigates Enhanced mRNA Translation Associated with the Metastatic Phenotype of Osteosarcoma Cells In Vivo", Jun. 24, 2016.

Myers, et al. "Fucose-Deficient Hematopoietic Stem Cells Have Decreased Self-Renewal and Aberrant Marrow Niche Occupancy", Transfusion. Dec. 2010 ; 50(12): 2660-2669.

Lu, et al., "VCAM-1 Promotes Osteolytic Expansion of Indolent Bone Micrometastasis of Breast Cancer by Engaging a4b1-Positive Osteoclast Progenitors", Cancer Cell 20, 701-714, Dec. 13, 2011.

Mandl, et al., Quantification of lymph node transit times reveals differences in antigen surveillance strategies of naïve CD4+ and CD8+ T cells, Oct. 30, 2012.

Lizotte, et al., "In situ vaccination with cowpea mosaic virus nanoparticles suppresses metastatic cancer", Dec. 21, 2015.

Lious, et al., "Intravital Imaging of the Mouse Popliteal Lymph Node", Feb. 2012.

Lathia, et al., "Direct In Vivo Evidence for Tumor Propagation by Glioblastoma Cancer Stem Cells", Sep. 2011, vol. 6, Issue 9.

Lin, et al., "Ectopic Expression of Vascular Cell Adhesion Molecule-1 as a New Mechanism for Tumor Immune Evasion", Cancer Res; 67: (4). Feb. 15, 2007.

Khanna, et al., "An orthotopic model of murine osteosarcoma with clonally related variants differing in pulmonary metastatic potential", Clinical & Experimental Metastasis 18: 261-271, 2000.

Kleinschmidt-DeMasters, "Progressive Multifocal Leukoencephalopathy Complicating Treatment with Natalizumab and Interferon Bet-1a for Multiple Sclerosis", Jul. 28, 2005.

Hayashi, et al., "Real-time Imaging of Tumor-Cell Shedding and Trafficking in Lymphatic Channels", Cancer Res 2007; 67: (17). Sep. 1, 2007.

Huang, et al., "The immunodominant major histocompatibility complex class I-restricted antigen of a murine colon tumor derives from an endogenous retroviral gene product", Proc. Natl, Acad, Sci., vol. 93, pp. 9730-9735, Sep. 1996.

Dorand, et al., "Cdk5 disruption attenuates tumor PD-L1 expression and promotes antitumor immunity", Jul. 22, 2016 • vol. 353 Issue 6297.

Germain, et al., "An extended vision for dynamic high-resolution intravital immune imaging", Semin Immunol. Dec. 2005 ; 17(6): 431-441.

Clifford, et al., "Natalizumab-associated progressive multifocal leukoencephalopathy in patients with multiple sclerosis: lessons from 28 cases", Lancet Neurol. Apr. 2010;9(4):438-46.

Ding, et al., "Association of VCAM-1 overexpression with oncogenesis, tumor angiogenesis and metastasis of gastric carcinoma", World J Gastroenterol Jul. 15, 2003 vol. 9 No. 7.

Chen, et al., "Macrophage Binding to Receptor VCAM-1 Transmits Survival Signals in Breast Cancer Cells that Invade the Lungs", Cancer Cell 20, 538-549, Oct. 18, 2011.

Bruckman, et al., "Dual-Modal Magnetic Resonance and Fluorescence Imaging of Atherosclerotic Plaques in Vivo Using VCAM-1 Targeted Tobacco Mosaic Virus", Nano Lett 2014, 14, 1551-1558.

Castellino, et al., "Chemokines enhance immunity by guiding naive CD81 T cells to sites of CD41 T cell—dendritic cell interaction", vol. 440, Apr. 13, 2006.

Barkauskas, et al., "Extravascular CX3CR1+ Cells Extend Intravascular Dendritic Processes into Intact Central Nervous System Vessel Lumen", Microsc Microanal. Aug. 2013 ; 19(4): 778-790.

Antezana, et al., "Natalizumab-induced hepatic injury: A case report and review of literature", Mult Scler Relat Disord. Nov. 2015;4(6):495-8.

Zhao, et al., "NKD2, a negative regulator of Wnt signaling, suppresses tumor growth and metastasis in osteosarcoma", Oncogene (2015) 34, 5069-5079.

* cited by examiner

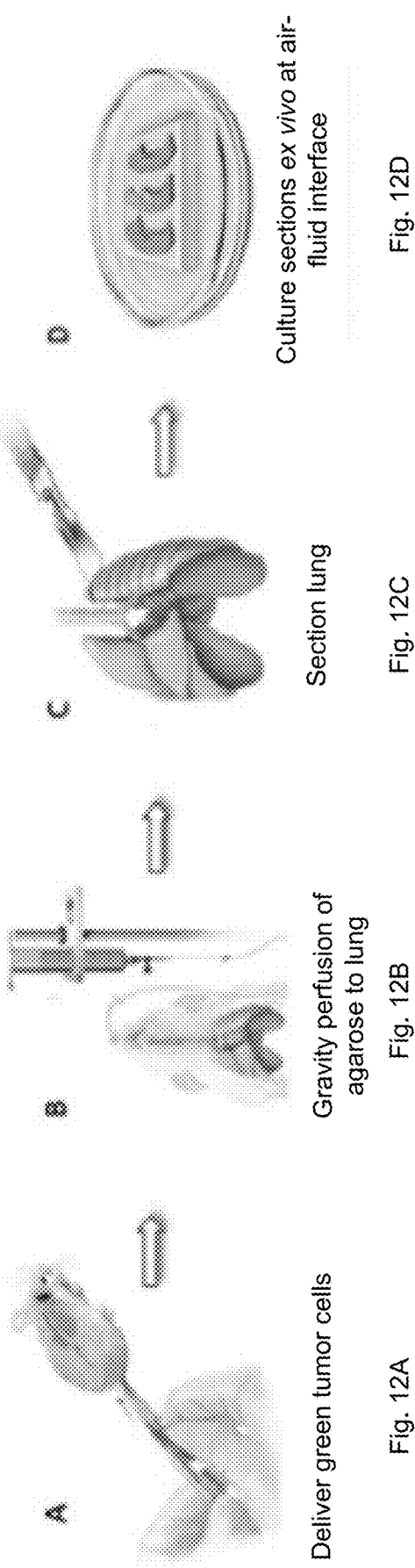

Representative H&E histology

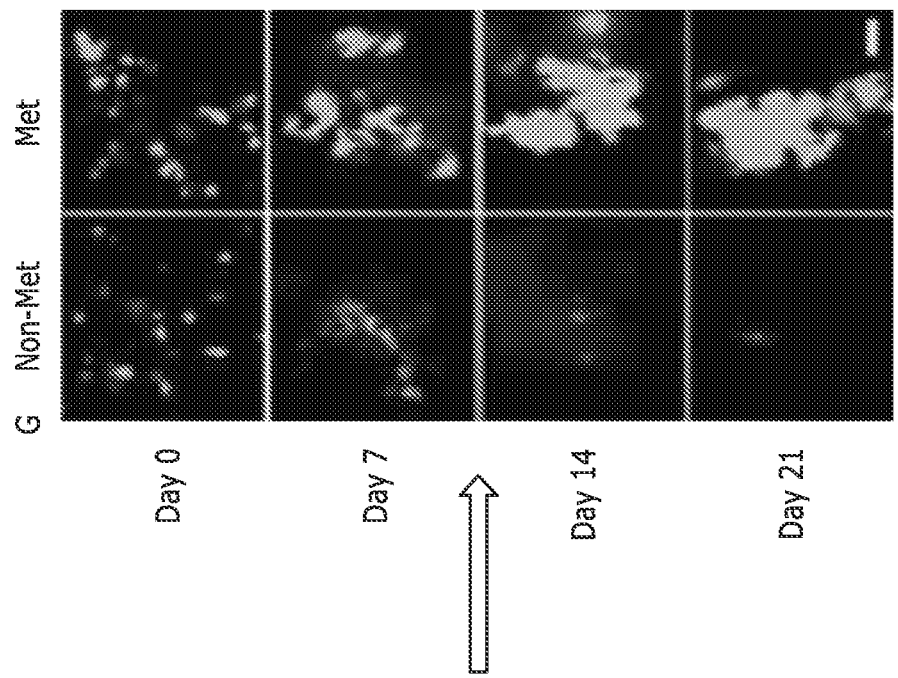
Fig. 12G Longitudinal Imaging Of Tumor-Microenvironment Interaction
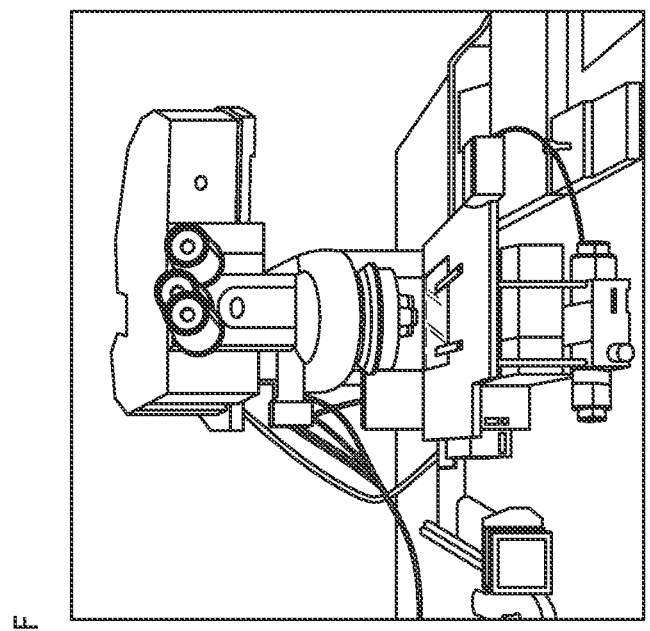
Fig. 12F Fluorescent Imaging Microscope

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic Construct

<400> SEQUENCE: 1

Val His Pro Lys Gln His Arg
1               5
```

COMPOSITIONS AND METHODS OF TREATING SARCOMA LUNG METASTASIS

RELATED APPLICATION

This application claims priority from U.S. Provisional Application No. 62/525,080, filed Jun. 26, 2017, the subject matter of which is incorporated herein by reference in its entirety.

BACKGROUND

Osteosarcoma (OS) is the most prevalent aggressive malignant bone cancer affecting children and young adults, with a predilection in boys and African American descent. OS arises from primitive mesenchymal bone-forming cells and has a high propensity for lung metastasis, accounting for >80% of all OS metastatic sites. Roughly 20% of the patients presents with pulmonary metastasis (pOS) initially at diagnosis, and up to 30% of patients presenting with localized disease will relapse in distant sites, including >80% metastatic relapses in the lung. Outcome for metastatic disease remains dismal (<30%) over the last 3 decades, which accounts for almost all of OS-related mortality. OS contains complex genetic alterations, making molecular targeted therapy challenging.

SUMMARY

Embodiments described herein relate to methods, compositions, and combination therapies for treating pulmonary metastasis of osteosarcoma cells (pOSs) and/or inhibiting growth of pOSs. It was found that VCAM-1 over-expression by pOS establishes a metastatic tumor niche in the lung tissue through its interaction with $\alpha4\beta1$ (VLA4) integrin on lung macrophages (MACs). Compared to non-metastatic parental murine high-grade OS tumor (K7), pOS cells $(K_7M_2)^3$ express high surface VCAM-1, which confers the metastatic phenotype in vivo. These observations make VCAM-1/$\alpha4\beta1$ potentially a set of high-impact target for treating pOS. Furthermore, we found that depleting pulmonary MACs, the major source of VCAM-1 ligand in the lung, abrogated pOS disease. Accordingly, pOSs can be treated by interfering with VCAM-1/$\alpha4\beta1$ signaling between pOS and MACs, by down-regulating VCAM-1 expression of pOS, depleting pulmonary MACs, or blocking VCAM-1/$\alpha4\beta1$ signaling in MACs.

Accordingly, in some embodiments, a method for inhibiting pOS, and/or metastases or metastatic spread in a subject with osteosarcoma can include administering to the subject a therapeutic agent that interferes with VCAM-1/$\alpha4\beta1$ signaling between pOS and MACs, down-regulates VCAM-1 expression of pOS, depletes MACs, and/or blocks VCAM-1/$\alpha4\beta1$ signaling in MACs in an amount sufficient to inhibit pOSs growth, and/or metastases, and/or metastatic spread.

In some embodiments, the therapeutic agent includes at least one of a macrophage depletion compound, a VCAM-1/$\alpha4\beta1$ integrin inhibitor, an inhibitory anti-VCAM peptide (iVCAM-1p), an anti-$\alpha4\beta1$ antibody, or an anti-$\alpha4\beta1$ inhibitor.

In other embodiments, the therapeutic agent includes at least one of a liposomal clodronate (Clophosome-A), an anti-$\alpha4\beta1$ antibody monoclonal antibody (e.g., natalizumab), a small molecule inhibitor of $\alpha4$ integrin, or iVCAM-1p (VHPKQHR (SEQ ID NO: 1).

In still other embodiments, the therapeutic agent can be administered by intranasal or inhalation in, for example, a nebulized or inhaled formulation.

In a further embodiment, the therapeutic agent can be administered alone or in combination with other cancer modalities in a multimodality format. For example, the above method can be further combined with such cancer modalities as regional chemotherapy infusion, systemic chemotherapy, or immunotherapy. The chemotherapeutic agent can be any one or more of the following: dacarbazine, carmustine, lomustine, tauromustine, fotemustine, semustine, cisplatin, carboplatin, vincristine, vinblastine, vindesine, taxol, dibromodulcitol, detorubicin, piritrexim and interferon (e.g., interferon-a2).

BRIEF DESCRIPTION OF THE DRAWINGS

FIGS. 12A-G illustrate ex vivo pulmonary OS metastasis assay. (A) GFP-tagged OS are seeded to lung via i.v. or intratibial injection. (B) Lungs are insufflated with agarose to preserve architecture, followed by sectioning (C). (D) Lung sections are grown at air-fluid interface, and validated by H&E for tissue integrity (E). (F) Lung cultures are imaged with 2P-LSM. (G) Images showing metastatic (Met) OS growth (right) and failure of non-metastatic (Non-met) OS growth (left) over 21 days in ex vivo culture.

DETAILED DESCRIPTION

Figure 1:
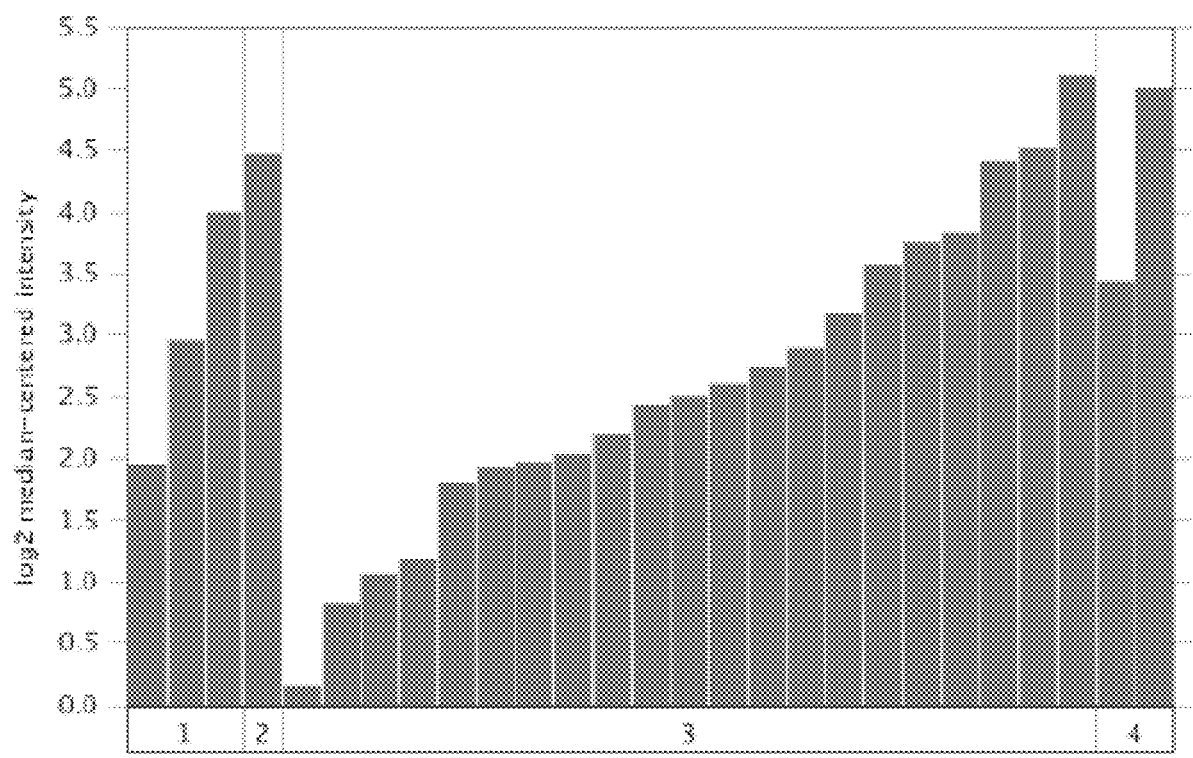
FIG. 1 illustrates the majority of clinical OS samples over-express VCAM-1. Search of Oncomine database revealed that 41 of 49 human OS samples showed increased VCAM-1 expression. 1, Chondroblasti OS; 2, Fibroblastic OS; 3, Osteoblastic OS; 4, Telangiectatic OS.

For convenience, certain terms employed in the specification, examples, and appended claims are collected here. Unless defined otherwise, all technical and scientific terms used herein have the same meaning as commonly understood by one of ordinary skill in the art to which this invention belongs.

As used herein, "one or more of a, b, and c" means a, b, c, ab, ac, bc, or abc. The use of "or" herein is the inclusive or.

As used herein, "protein" is a polymer consisting of the 20 amino acids. Although "polypeptide" is often used in reference to relatively large polypeptides, and "peptide" is often used in reference to small polypeptides, usage of these terms in the art overlaps and is varied.

The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

The term "mutant" refers to changes in the genetic material of an organism, in particular a change (i.e., deletion, substitution, addition, or alteration) in a wild type polynucleotide sequence or changes in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well.

"Homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into a target tissue (e.g., the central nervous system), such that it enters the animal's system and, thus, is subject to metabolism and other like processes, for example, subcutaneous administration.

By "natalizumab" or "Tysabri" is meant a humanized antibody against VLA-4 as described in U.S. Pat. Nos. 5,840,299 and 6,033,665, which are herein incorporated by reference in their entirety. Also contemplated herein are other VLA-4 specific antibodies. Such anti-VLA-4 antibodies and immunoglobulins include but are not limited to those immunoglobulins described in U.S. Pat. Nos. 6,602,503 and 6,551,593, published U.S. Application No. 20020197233. Preparation of the antibody can be by the methods disclosed in these patents and applications, by mammalian cell expression, or via transgenic animal expression systems (e.g., goat).

Embodiments described herein relate to methods, compositions, and combination therapies for treating pulmonary metastasis of osteosarcoma cells (pOSs) and/or inhibiting growth of pOSs. It was found that VCAM-1 over-expression by pOS establishes a metastatic tumor niche in the lung tissue through its interaction with $\alpha 4\beta 1$ (VLA4) integrin on lung macrophages (MACs). Compared to non-metastatic parental murine high-grade OS tumor (K7), pOS cells $(K_7M_2)^3$ express high surface VCAM-1, which confers the metastatic phenotype in vivo. These observations make VCAM-1/$\alpha 4\beta 1$ potentially a set of high-impact target for treating pOS. Furthermore, we found that depleting pulmonary MACs, the major source of VCAM-1 ligand in the lung, abrogated pOS disease. Accordingly, pOSs can be treated by interfering with VCAM-1/$\alpha 4\beta 1$ signaling between pOS and MACs, by down-regulating VCAM-1 expression of pOS, depleting pulmonary MACs, or blocking VCAM-1/$\alpha 4\beta 1$ signaling in MACs.

In at least some pulmonary osteosarcoma cells expressing VCAM-1, therapeutic agents that target and reduce and inhibit the VCAM-1/$\alpha 4\beta 1$ signaling within pulmonary macrophage cells can be used to inhibit one or more of the growth, proliferation, and/or metastases of these pulmonary metastasis osteosarcoma cells (pOSs).

Accordingly, in some embodiments, a method for inhibiting pOS, and/or metastases or metastatic spread in a subject with osteosarcoma can include administering to the subject a therapeutic agent that interferes with VCAM-1/$\alpha 4\beta 1$ signaling between pOS and MACs, down-regulates VCAM-1 expression of pOS, depletes MACs, and/or blocks VCAM-1/$\alpha 4\beta 1$ signaling in MACs in an amount sufficient to inhibit pOSs growth, and/or metastases, and/or metastatic spread.

As used herein, a therapeutic agent that interferes with VCAM-1/$\alpha 4\beta 1$ signaling between pOS and MACs, down-regulates VCAM-1 expression of pOS, depletes MACs, and/or blocks VCAM-1/$\alpha 4\beta 1$ signaling in MACs refers to a composition comprised of a substance that decreases and/or suppresses VCAM-1/$\alpha 4\beta 1$ signaling between pOS and MACs, down-regulates VCAM-1 expression of pOS, depletes MACs, and/or blocks VCAM-1/$\alpha 4\beta 1$ signaling in MACs to decrease and/or suppress cancer cell metastasis. The decrease in VCAM-1/$\alpha 4\beta 1$ signaling between pOS and MACs, down-regulation of VCAM-1 expression of pOS, depletion of MACs, and/or blocking of VCAM-1/$\alpha 4\beta 1$ signaling in MACs can be facilitated in several ways including: direct inhibition of the activity of the VCAM-1/$\alpha 4\beta 1$ signaling (e.g., by using neutralizing antibodies, small molecules or peptidomimetics, dominant negative polypeptides, (e.g., Natalizumab, AJM300, ELND002); inhibition of genes that express the VCAM-1 and/or $\alpha 4\beta 1$ (e.g., by blocking the expression or activity of the genes and/or proteins); activation of genes and/or proteins that inhibit one or more of, activity and function of VCAM-1 and/or $\alpha 4\beta 1$ (e.g., by increasing the expression or activity of the genes and/or proteins); inhibition of genes and/or proteins that are downstream mediators of VCAM-1 and/or $\alpha 4\beta 1$ (e.g., by blocking the expression and/or activity of the mediator genes and/or proteins); introduction of genes and/or proteins that negatively regulate one or more of, activity and function of VCAM-1 and/or $\alpha 4\beta 1$ (e.g., by using recombinant gene expression vectors, recombinant viral vectors or recombinant polypeptides); gene replacement with, for instance, a hypomorphic mutant of VCAM-1 and/or $\alpha 4\beta 1$ (e.g., by homologous recombination, overexpression using recombinant gene expression or viral vectors, or mutagenesis), and/or depletion of pulmonary MAC.

In certain embodiments, the therapeutic agent can bind to, complex with, and/or act as a steric or competitive inhibitor of the VCAM-1 and/or $\alpha 4\beta 1$. Competitive inhibitors refer to proteins or polypeptides that inhibit the bioactivity of the endogenous, wild type form of the protein (i.e., VCAM-1 and/or $\alpha 4\beta 1$). As a result, a competitive inhibitor of VCAM-1 and/or $\alpha 4\beta 1$ can inhibit the normal functions of VCAM-1 and/or $\alpha 4\beta 1$ and inhibit cancer cell growth.

In other embodiments, the therapeutic agent can specifically bind to or complexes with VCAM-1 and/or α4β1 that is expressed by pOSs. The therapeutic agent can be an antibody, such as a monoclonal antibody, a polyclonal antibody, or a humanized antibody. The antibody can include Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule. By way of example, the antibody or fragment thereof can specifically or selectively bind to α4β1 antibody (e.g., natalizumab).

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate an antibody or fragment thereof specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody system (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

In some embodiments, the antibody can be an anti-α4β1 monoclonal antibody, such as natalizumab. In other embodiments, the antibody can be a VCAM-1 antibody, such as described, for example, in U.S. Pat. No. 7,655,417 and U.S. Patent Publication No. 2015/0125878, which are incorporated by reference in their entirety.

In other embodiments, the agent (or therapeutic agent) that binds to or complexes with VCAM-1 and/or α4β1, such as VCAM-1 expressed by a pulmonary cancer cell or α4β1 expressed by a pulmonary macrophage, can include a peptide or small molecule that binds to and/or complexes with VCAM-1 and/or α4β1. In one example, the therapeutic agent binds to or complexes with VCAM-1 and/or α4β1. In some embodiments, the peptide can include an inhibitory anti-VCAM peptide (iVCAM-1p) or a an inhibitory anti-VCAM peptide (iVCAM-1p) substantially homologous to iVCAM-1p (VHPKQHR (SEQ ID NO: 1). By substantially homologous, it is meant the peptide has at least about 80%, about 90%, about 95%, about 96%, about 97%, about 98%, about 99% or about 100% sequence identity with a portion of the amino acid sequence of the iVCAM-1p (VHPKQHR (SEQ ID NO: 1).

One or more of, the peptides described herein can also be modified by natural processes, such as posttranslational processing, and/or by chemical modification techniques, which are known in the art. Modifications may occur in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Other type of peptide modifications may include for example, amino acid insertion (i.e., addition), deletion and substitution (i.e., replacement), either conservative or nonconservative (e.g., D-amino acids) in the polypeptide sequence where such changes do not substantially alter the overall competitive inhibitor ability of the polypeptide.

Peptides and/or proteins described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. The peptides and/or proteins of this application may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell.

The purification of the peptides and/or proteins may be done by affinity methods, ion exchange chromatography, size exclusion chromatography, hydrophobicity or other purification technique typically used for protein purification. The purification step can be performed under non-denaturating conditions. On the other hand, if a denaturating step is required, the protein may be renatured using techniques known in the art.

In another embodiment, the agent, which inhibits interaction or signaling of VCAM-1 and/or α4β1 described in this application, can include an agent that reduces or inhibits VCAM-1 expression in the cancer cells to inhibit cancer growth and/or metastasis. "Expression", means the overall flow of information from a gene to produce a gene product (typically a protein, optionally post-translationally modified or a functional/structural RNA).

The agent can include an RNAi construct that inhibits or reduces expression of the VCAM-1 in the cancer cell. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, *Nucleic Acids Res,* 25:776-780; *J Mol Recog* 7:89-98;

*Nucleic Acids Res* 23:2661-2668; *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (*Proc Natl Acad Sci USA*, 98:9742-9747; *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, *Genes Dev*, 2002, 16:948-58; Nature, 2002, 418:38-9; *RNA*, 2002, 8:842-50; and *Proc Natl Acad Sci*, 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the VCAM-1 in a cancer cell. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the VCAM-1 expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in *E. coli* strain DH5α cells. After positive clones are selected, plasmid can be transfected into 293T cells by calcium precipitation. The viral supernatant collected containing shRNA can then be used to infect mammalian cells in order to down regulate the VCAM-1.

In another embodiment, the therapeutic agent can include antisense oligonucleotides. Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., VCAM-1).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556;

*Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma virus (*Cell* 22:787-797), the herpes thymidine kinase promoter (*Proc Natl Acad Sci* 78:1441-1445), the regulatory sequences of the metallothionein gene (*Nature* 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route.

In still other embodiments, the therapeutic agent can include a macrophage depletion agent that is administered to the subject, for example, by intranasal administration or inhalation, to delete pulmonary macrophages.

The term macrophage depletion refers to the process of reducing in a large amount but not totally the circulating and tissue macrophages. A convenient range of remaining macrophages after treatment is 0% to 50%. A particular range of remaining macrophages is 0% to 20%.

Macrophage number can be reduced by administrating, in the subject, antagonists of macrophages, such as toxic substances, like cis-platinium, or antibodies, altering macrophage development or function and finally killing them. The administration of antagonists is performed by well-known techniques, including the use of liposomes. The reduction of macrophages can also be reached by irradiation.

In a particular embodiment, the macrophage depletion is obtained by injecting liposomes containing $Cl_2MDP$ or clodronate-loaded liposomes (e.g., Clophosome) according to the technique of Van Rooijen et al. (Van Rooijen N. 1989. J. Immunol. Methods 124, 1-6). The liposome size can range from 0.5 to 7 µm to be ingested by pulmonary macrophages, resulting in their killing.

In some embodiments, the agents can be provided in a pharmaceutical composition. The pharmaceutical compositions can include a pharmaceutically effective amount of the agents described above and a pharmaceutically acceptable diluent or carrier.

The term "pharmaceutically acceptable carrier", "diluents", "adjuvant" and "physiologically acceptable vehicle" and the like are to be understood as referring to an acceptable carrier or adjuvant that may be administered to a patient, together with an agent of this invention, and which does not destroy the pharmacological activity thereof. Further, as used herein "pharmaceutically acceptable carrier" or "pharmaceutical carrier" are known in the art and include, but are not limited to, 0.01-0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

In addition, the term "pharmaceutically effective amount" or "therapeutically effective amount" refers to an amount (dose) effective in treating a patient, having, for example, cancer, such as glioblastoma multiforme. It is also to be understood herein that a "pharmaceutically effective amount" may be interpreted as an amount giving a desired therapeutic effect, either taken into one dose or in a dosage or route or taken alone or in combination with other therapeutic agents. A "pharmaceutically effective amount" may be understood as an amount of the therapeutic agent effective to interfere with VCAM-1/α4β1 signaling between pOS and MACs to inhibit cancer cell growth and/or metastasis.

Determination of a therapeutically effective amount is within the capability of those skilled in the art. The exact formulation, route of administration and dosage can be chosen by the individual physician in view of the patient's condition.

Pharmaceutical compositions described herein can be administered in a suitable pharmaceutical carrier by one of several routes, which include direct injection, and topical application. Formulations of the compositions will vary according to the route of administration selected (e.g., solution or emulsion).

In another embodiment, the therapeutic agent can be conjugated to a nanoparticle. For example, the therapeutic peptide to VCAM-1 can be linked to a viral nanoparticle carrier to facilitate delivery of the peptide to the pOSs by, for example, inhalation and/or intranasal delivery. The viral nanoparticle can include a plant virus or virus like particle.

In some embodiments, plant virus or virus like particle can be a filamentous plant virus or virus like particle. The filamentous plant virus belongs to a specific virus family, genus, or species. For example, in some embodiments, the filamentous plant virus belongs to the Alphaflexiviridae family. The Alphaflexiviridae family includes the genus *Allexivirus, Botrexvirus, Lolavirus, Mandarivirus, Potexvirus*, and *Sclerodamavirus*. In some embodiments, the filamentous plant virus belongs to the genus *Potexvirus*. In further embodiments, the filamentous plant virus belongs to the Potato Virus X species.

In other embodiments, the plant virus or virus like particle can be a rod-shaped plant virus. A rod-shaped plant virus is a virus that primarily infects plants, is non-enveloped, and is shaped as a rigid helical rod with a helical symmetry. Rod shaped viruses also include a central canal. Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus belongs to a specific virus family, genus, or species. For example, in some embodiments, the rod-shaped plant virus belongs to the Virgaviridae family. The Virgaviridae family includes the genus *Furovirus, Hordevirus, Pecluvirus, Pomovirus, Tobamovirus*, and *Tobravirus*. In some embodiments, the rod-shaped plant virus belongs to the genus *Tobamovirus*. In further embodiments, the rod-shaped plant virus belongs to the tobacco mosaic virus species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are about 300 nm in length and about 18 nm in diameter. Negatively stained electron microphotographs show a distinct inner channel of about 4 nm.

In still other embodiments, the plant virus or virus like particle is an icosahedral plant virus. Examples of icosahedral plant viruses include the virus families Geminiviridae, Luteoviridae, Bromoviridae, Phycodnaviridae, and Picornaviridae. In some embodiments, the icosahedral plan virus is from the family Picornaviridae. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily. Examples of viruses from the Comovirinae subfamily include Cowpea mosaic virus, Broad bean wilt virus 1, and Tobacco ringspot virus. In a further embodiment, the virus particles are from the Genus *comovirus*. A preferred example of a *comovirus* is the cowpea mosaic virus particles.

The therapeutic peptide can be conjugated to the surface of the nanoparticle via, for example, a PEG spacer (e.g., 1,000 Da) to a functional group pre-conjugated to the nanoparticle. The PEG spacer is designed to reduce the steric hindrance of the drug carrier and to achieve effective specific binding to the target. The therapeutic peptide can be conjugated to the nanoparticle via, for example, a disulfide spacer. The disulfide spacer can be designed to release the therapeutic peptide in cytoplasm, which has a high concentration of reductive glutathione (e.g., about 3 mM). The disulfide spacer can be readily reduced by cytoplasmic glutathione to release the therapeutic peptide inside cancer cells.

In some embodiments, the nanoparticle comprising the therapeutic peptide can be directly or indirectly labeled with a detectable moiety or imaging agent. The role of a detectable moiety is to facilitate the detection step of a nanoparticle by allowing visualization of the complex formed by binding of the therapeutic peptide to the cancer cell. The detectable moiety can be selected such that it generates a signal, which can be measured and whose intensity is related (preferably proportional) to the amount of the nanoparticle bound to the tissue being treated. Methods for labeling biological molecules, such as polypeptides and antibodies are well-known in the art (see for example, *Methods in Enzymol.*, 1974, Vol. 34, Academic Press: New York, N.Y.; and, *Anal. Biochem.*, 1988, 171: 1-32).

In still other embodiment, the therapeutic agent or a pharmaceutical composition comprising the therapeutic agent can be administered to pOSs in the airways or respiratory tract, by intranasal or inhalation administration. Intranasal or inhalation administration of the therapeutic agent can be more effective to treat the pOSs therapeutically or prophylactically than alternative means of administration, such as IP administration. Inhalation and/or intranasal delivery and administration is superior, more efficacious and effective at lower doses than systemic administration (IV or IP) of the same therapeutic agent in the same amounts.

Administration to the airways or respiratory tract may be by any recognized or known means and may include inhalation administration or intranasal administration. For enhanced effectiveness, the therapeutic agent can be delivered to one or more of the upper respiratory tract and the lower respiratory tract, and may include the nasal cavity, nose, sinus, throat, pharynx, larynx, trachea, bronchi and the lungs.

Inhalation refers to taking in, particularly in the context of taking in or administering/being administered an agent or a composition comprising such, whereby the agent is delivered to the respiratory tract. The respiratory tract may include the upper and, or, and/or lower respiratory tract. The upper respiratory tract comprises the nose, nasal cavity, sinuses, larynx, trachea. The lower respiratory tract comprises the lungs, airways (bronchi and bronchioles) and air sacs (alveoli). Inhalation may occur via the nose or via the mouth, or via direct administration to the lower respiratory tract as in intratracheal administration. Thus, inhalation may include nose only or primarily, intranasal, inhaling via the mouth, oral inhalation, intratracheal inhalation, intratracheal instillation. Thus inhalation provides for and contemplates any means of administration whereby agent reaches or is deposited at or in the respiratory tract exclusively, specifically or preferentially, including the upper and/or lower respiratory tract.

The term intranasal as used herein includes, but is not limited to, administering, administration or occurring within or via the nose or nasal structures. The term intranasal as used herein and as exemplified as an embodiment in the examples in not intended to be limited to or to imply limitation to administration directly or specifically or solely via the nose or nasal cavity, particularly in serving to exclude other means of administration whereby agent is delivered or otherwise provided to, deposited in or at or otherwise distributed to the respiratory tract.

Devices for administration or delivery to the respiratory tract or airway(s) are known and recognized in the skilled art and in clinical or medical practice and are applicable in the methods, protocols and compositions of the present invention. Devices include the metered dose inhaler, metered spray pumps, hand-bulb atomizer, small or large volume nebulizers, ultrasonic nebulizer and dry powder inhaler.

In a further embodiment, the therapeutic agent can be used in combination and adjunctive therapies for inhibiting cancer cell proliferation, growth, and motility. The phrase "combination therapy" embraces the administration of a therapeutic agent, which interferes with VCAM-1/$\alpha 4\beta 1$ signaling between pOS and MACs to inhibit cancer cell growth and/or metastasis, and an additional therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). The phrase "adjunctive therapy" encompasses treatment of a subject with agents that reduce or avoid side effects associated with the combination therapy of this application.

A combination therapy is intended to embrace administration of these therapeutic agents in a sequential manner, that is, wherein different therapeutic agents are administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of therapeutic agents can be effected by an appropriate routes including, but not limited to, oral routes, intravenous routes, intramuscular routes, and direct absorption through mucous membrane tissues. The therapeutic agents can be administered by the same route or by different routes. The sequence in which the therapeutic agents are administered is not narrowly critical.

Combination therapy also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at a suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments the therapeutic agent, which interferes with VCAM-1/$\alpha 4\beta 1$ signaling between pOS and MACs to inhibit cancer cell growth and/or metastasis, can be administered in combination at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agents available in commercial use, in clinical evaluation and in pre-clinical development, which could be included in this application by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

The following example is included to demonstrate different embodiments of the invention. It should be appreciated by those of skill in the art that the techniques disclosed in the examples, which follow represent techniques discovered by the inventor to function well in the practice of the claimed embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the claims.

Example

The data discussed herein implicate that VCAM-1 overexpression by osteosarcoma pulmonary metastasis (pOS) is a critical step in establishing a metastatic tumor niche in the lung tissue through its interaction with $\alpha 4\beta 1$ (VLA4) integrin on lung macrophages (MACs). As our data indicate, compared to non-metastatic parental murine high-grade OS tumor (K7), pOS cells $(K_7M_2)^3$ express high surface VCAM-1, which confers the metastatic phenotype in vivo. This and other associated findings suggest that VCAM-1 plays a similarly crucial role in pOS as seen in metastatic breast cancer and immune-resistant cervical cancer. These observations make VCAM-1/$\alpha 4\beta 1$ potentially a set of high-impact target for treating pOS. Furthermore, we found that depleting pulmonary MACs, the major source of VCAM-1 ligand in the lung, abrogated pOS disease. To our knowledge, this is the first surface marker in pOS that can be targeted in future clinical translational immunotherapy. We have also identified a murine OS-specific tumor-associated antigen and a cytotoxic T cell line specific for this antigen, making it possible to interrogate the interplay between VCAM-1 signaling and T-cell mediated immunotherapy for OS. Additionally, as FDA has approved anti-α4 blocking antibody (Natalizumab) for treating T-cell mediated autoimmune diseases, this proposal creates an opportunity for IND-enabling pre-clinical studies to show feasibility and efficacy of targeting pulmonary MACs through intranasal, intra-tracheal or inhalation routes of administrating anti-α4 blocking antibody (mAb) in pOS to avoid potential systemic toxicities. Therefore, we will examine how disruption of VCAM-1 mediated signaling affects pOS outcome in vivo. We hypothesize that interfering VCAM-1/α4β1 signaling between pOS and MACs by down-regulating VCAM-1, depleting MACs or blocking VCAM-1/α4β1 signaling will reduce pOS and improve overall disease-free survival. We will test this hypothesis with the following specific aims.

Characterize Functional Outcome of Disrupting MAC-Dependent Survival of pOS

We will strengthen the comparison of VCAM-1$^{lo}$ and VCAM-1$^{hi}$ K$_7$M$_2$ cell lines we have created for in vivo growth kinetics and associated immune responses in the lungs, and further expand our observation to include testing lung metastatic potential of other human and mouse pOS cell lines and patient-derived xenografts (PDXs) available through our own repository and that of our collaborator at Texas Children's Hospital. We will characterize phenotypic and functional outcomes of various myeloid and other immune cellular compartments in the lung tissue harboring VCAM-1$^{lo}$ and VCAM-1$^{hi}$ OS using cellular and molecular approaches, including lentiviral transduction to over-express VCAM-1 or silence VCAM-1 using shRNA or CRISPR/Cas9 approaches, and directly measuring cellular interactions between pOS and MACs in the lung with two-photon laser scanning microscopy (2P-LSM). We will use lineage-specific fluorescent reporter mice (CX3CR1$^{+/GFP}$; CCR2$^{+/}$$_{RFP}$; CD11b-CFP/DTR) in combination with differentially fluorescent labeled pOS VCAM-1$^{lo}$/VCAM-1$^{hi}$ variants to directly observe interaction and niche occupancy in live mouse lung and organotypic lung cultures. MACs will be depleted with intranasal (i.n.) liposomal clodronate or diphtheria toxin treatment of CD11b-DTR mice.

Functional Blockade of VCAM-1/α4β1 on the Outcome of pOS

This will be accomplished by disrupting VCAM-1/1/α4β1 signaling using VCAM-1 specific inhibitory peptide (iVCAM-1p) or i.n./intra-tracheal (i.tr.) administration of anti-α4 mAb, which is FDA-approved for autoimmune disease indications including multiple sclerosis and inflammatory bowel diseases. We set a goal to obtain pre-clinical, IND-enabling data for monitoring systemic and local toxicities and refining optimal dosing regimen using the FDA-approved anti-α4 antibody Natalizumab i.n., i.tr. or via nebulized inhalation to treat late-stage pOS.

Successful execution of this proposal will provide impactful insight into how pOS promote their invasion and survival in the lungs, and will lay the foundation for exploitation of VCAM-1 signaling in new immune approaches against pOS. Specifically, our data indicate that intranasal administrations of agents that deplete pulmonary MACS or block VCAM-1/α4β1 will have impactful therapeutic benefit in treating pOS. As liposomal clodronate is being tested in breast cancer and prostate cancer (NCT01291433; NCT00127205; NCT00216060), our data opens the possibility of using intranasal administration of liposomal clodronate as a therapy for pOS in childhood and AYA populations. In addition, anti-α4 integrin agent, Natalizumab, is FDA-approved for autoimmune disorders and in clinical trials for GVHD and stroke (e.g., NCT02325440; NCT02176031; NCT02730455; NCT02483845), and small molecule inhibitor against α4 integrin, AJM300 (Japan studies) and ELND002 (NCT01318421, NCT01144351; closed, awaiting results) are also in clinical trials for autoimmune conditions, paving the potential venue for their use in pOS.

The data presented hereafter shows previously un-appreciated high levels of VCAM-1 expression in the aggressive, metastatic murine OS model (K7M2) as compared to parental tumor (K7)[3], a finding that has also been shown in human OS (FIG. 1). Furthermore, our data show that depleting pulmonary MACs, the major source of VCAM-1 ligand in the metastatic tissue microenvironment, dramatically reduces the incidence of pOS. This finding represents one of the first key cell surface markers that differentiates the aggressive metastatic sub-population of OS from the bulk of localized, less metastatic-prone OS, and argues VCAM-1/α4β1 and pulmonary MACs as potential targets of immunotherapeutic targets against pOS.

Understanding the host immune response mechanism in cancer is a critical first step in clinical translation. The data described herein provides a strong rationale to target pulmonary MACS and VCAM-1 in pOS. A majority of clinical OS samples (41 of 49; 84%; FIG. 1) harbor VCAM-1 over-expression. These clinical data lend further support for the underlying rationale to target VCAM-1/α4β1 and MACs in pOS and the use of nebulized liposomal clodronate, inhibitory anti-VCAM-1 peptide (iVCAM-1p), anti-α4 mAb or anti-α4 integrin inhibitors (AJM300 and ELND002) in late-stage pOS patients to assess safety and toxicity, with a secondary end-point of measuring pOS response.

The identification of targetable molecular interactions and an immune cell subset as potential new therapies for the devastating pOS disease is highly innovative and exciting. The utilization of the sophisticated 2P-LSM to understand this process in intact tissues will provide novel insights into cellular and molecular interactions in this process that may lead to the identification of additional immuno-therapeutic or molecularly targeted treatment options for pOS.

Data

Figure 2A:
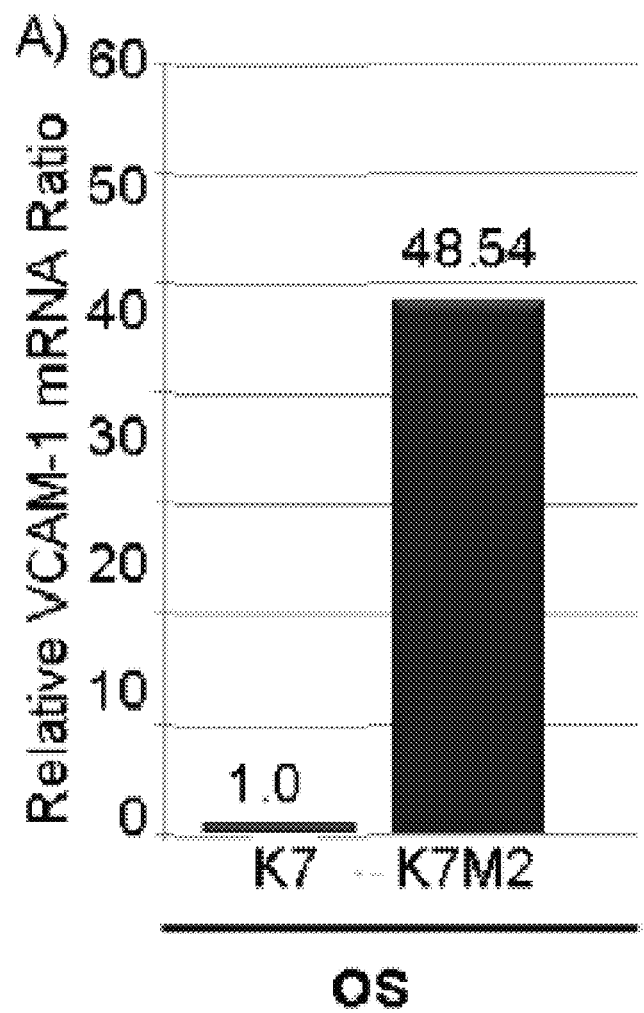
FIGS. 2A-B illustrate increased VCAM-1 expression in pOS. (A) qPCR was performed for VCAM-1 expression on OS cell lines. VCAM-1 mRNA level of K7 was used as a reference (relative mRNA level of 1.0). (B) Surface VCAM-1 expression in OS cell lines were assessed by flow cytometry.
Figure 2B:
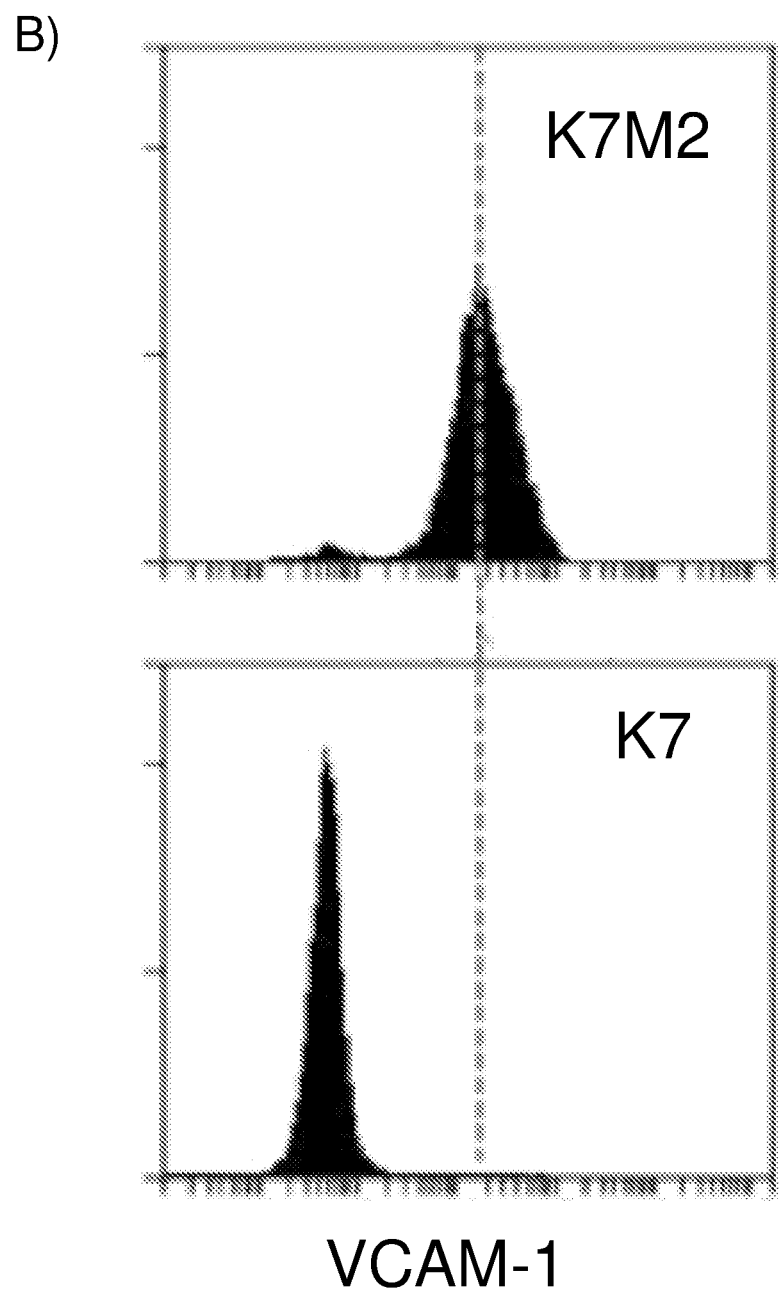
Figure 3A:
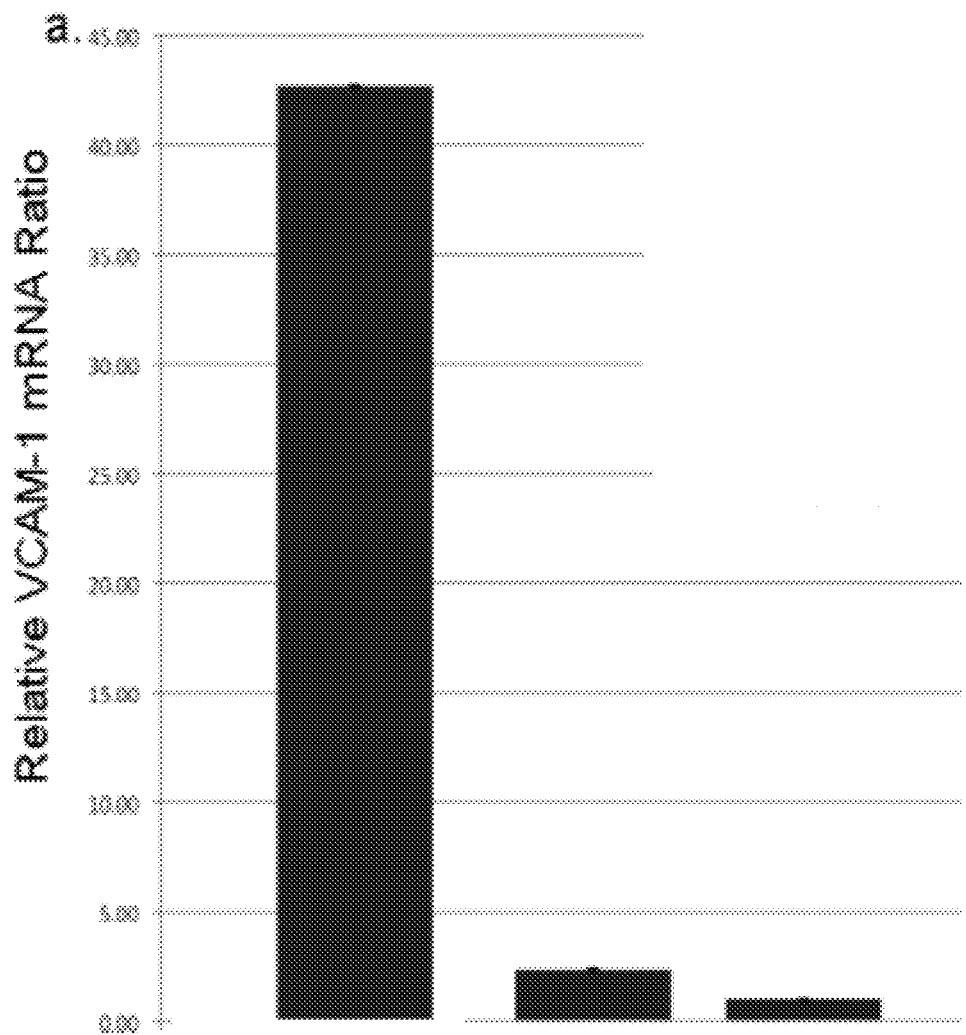
FIGS. 3A-B illustrate silencing of VCAM-1 gene transcripts in K7M2. (A) K7M2 cells were transduced with 5 lentiviral shRNA constructs designed to silence VCAM-1 transcript. Two of the 5shRNA constructs resulted in >80% silencing of VCAM-1 mRNA expression in K7M2 compared to non-silencing shRNA control. (B) Flow cytometry confirms reduced level of VCAM-1 expression in the shRNA knockdown cell lines (VCAM-1kd) compared to non-silencing control (VCAM-1NS).
Figure 3B:
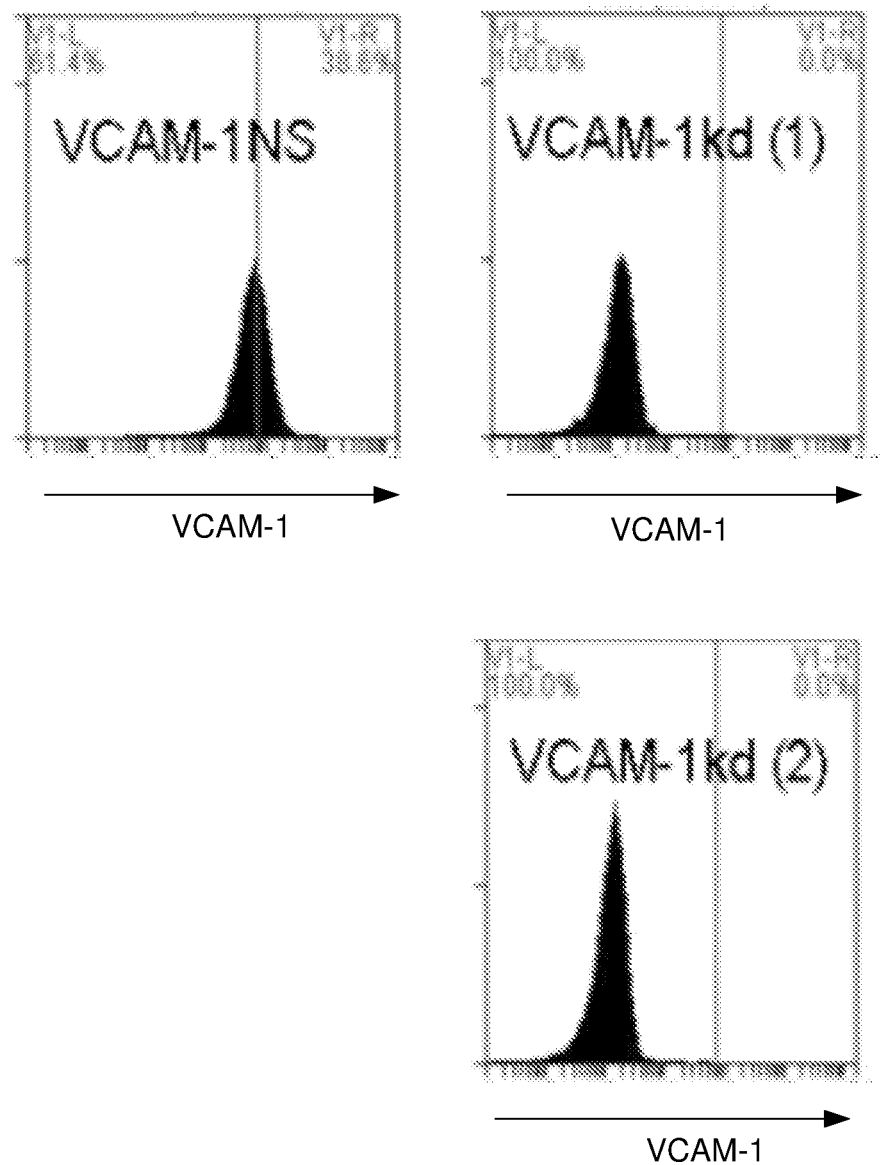

We utilized a pair of spontaneous, high-grade murine OS lines from Balb/c mouse (H-2$^d$), K7 and K7M2, where K7M2 is derived from in vivo K7 metastasis. Both tumors express AH1 mRNA, a peptide derived from MuLV gp70 first identified in murine colon tumors. Anti-AH1 CD8$^+$ T cell clones kill K7 and K7M2 in vitro (data not shown), demonstrating AH1 is a relevant tumor-associated antigen in this tumor system. We observed a dramatic increase in mRNA and protein levels of VCAM-1 in K7M2 compared to K7 in vitro (FIG. 2), mirroring findings in cervical cancer (CC)[4]. We then tested whether suppressing ectopic VCAM-1 on K7M2 could revert the metastatic behavior back to that of parental K7. We used 5 lentiviral shRNAs (with bi-cistronic GFP linked by IRES and a puromycin marker) to knockdown VCAM-1 mRNA and protein expression in K7M2 (VCAM-1kd). We also transduce K7M2 with a non-silencing shRNA as controls for off-target effect (VCAM-1NS). qPCR and FACS confirmed a knockdown efficiency of 80-90% in the VCAM-1kd lines (FIG. 3).

Figure 4A:
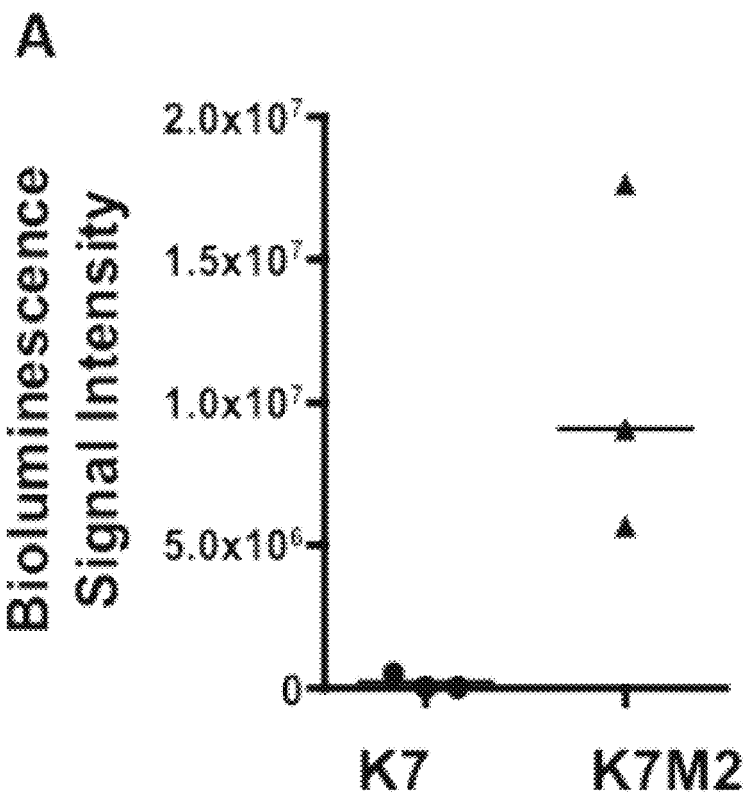
FIGS. 4A-C illustrate K7M2 preferentially metastasized to the lung in VCAM-1 dependent manner. $1\times10^6$ Luc-K7 or Luc-K7M2 were injected i.v. into Balb/c mice. Lung tissues were imaged on day 22 for bioluminescence signals (A) as well as extracted for quantitative assessment of the tumor-specific gp70 transcript (B). (C) $1\times10^6$ K7M2 VCAM-1NS and VCAM-1kd cells were injected i.v. into Balb/c mice, lungs harvested on day 22 for gp70 transcript by qRT-PCR.
Figure 4B:
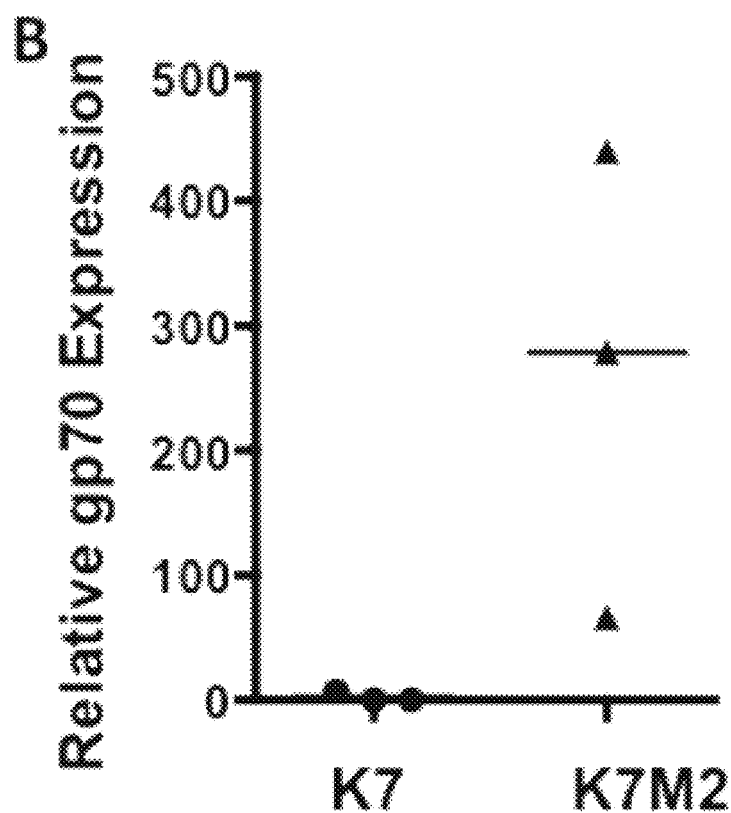
Figure 4C:
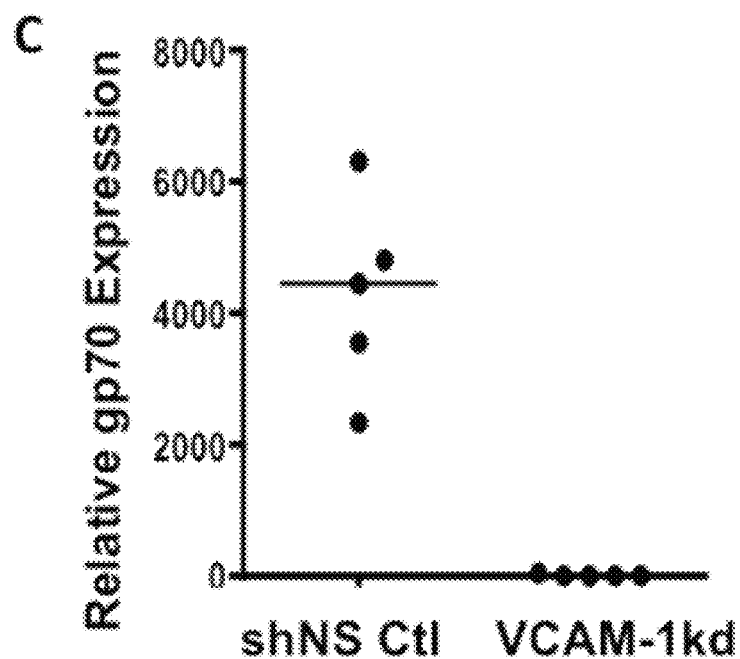
Figure 5A:
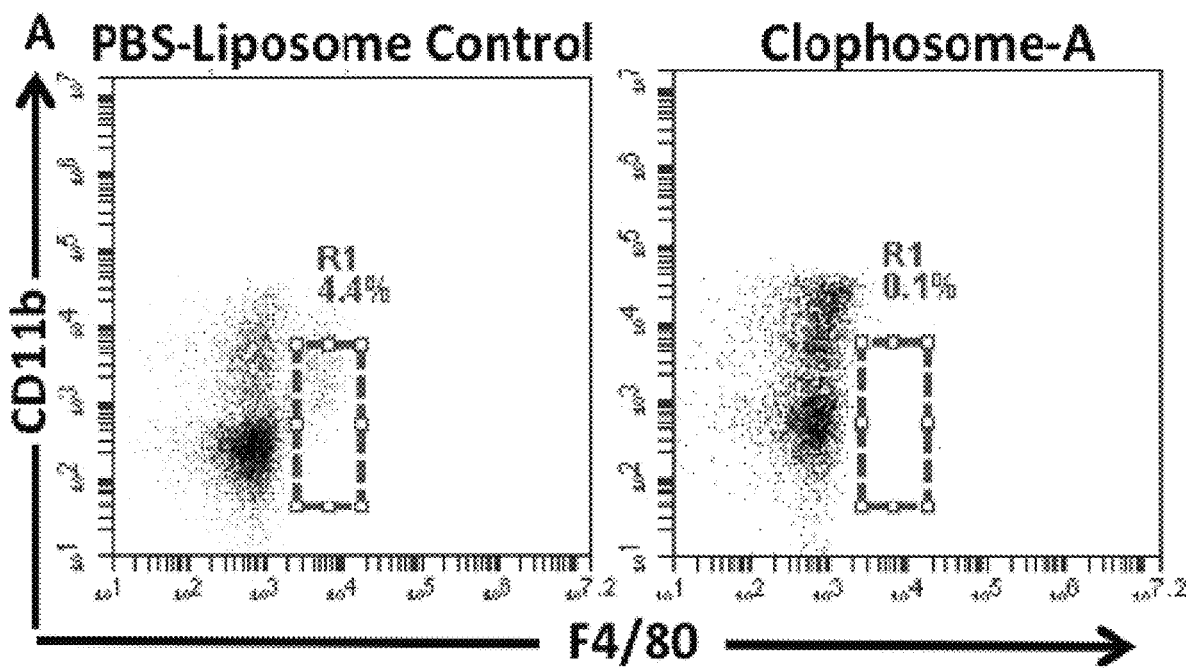
FIGS. 5A-C illustrate depletion of macrophages reduces metastatic OS. (A) Single intranasal administration of liposomal clondronate (Clophosome-A; right) resulted in near complete depletion of $CD11b^+/F4/80^+$ macrophages in the lungs of Balb/C mice 37 days following i.v. injection of live $5\times10$ luc-K7M2 (day 0) in mice receiving control intranasal liposome (left) or clophosome-A (right) on days −4 and −2. (C) Overall tumor incidence in the mouse lungs from (B), showing a complete absense of tumor in Clophosome-A group (open squares) as compared to 57% incidence in the control group (open circles).
Figure 5B:
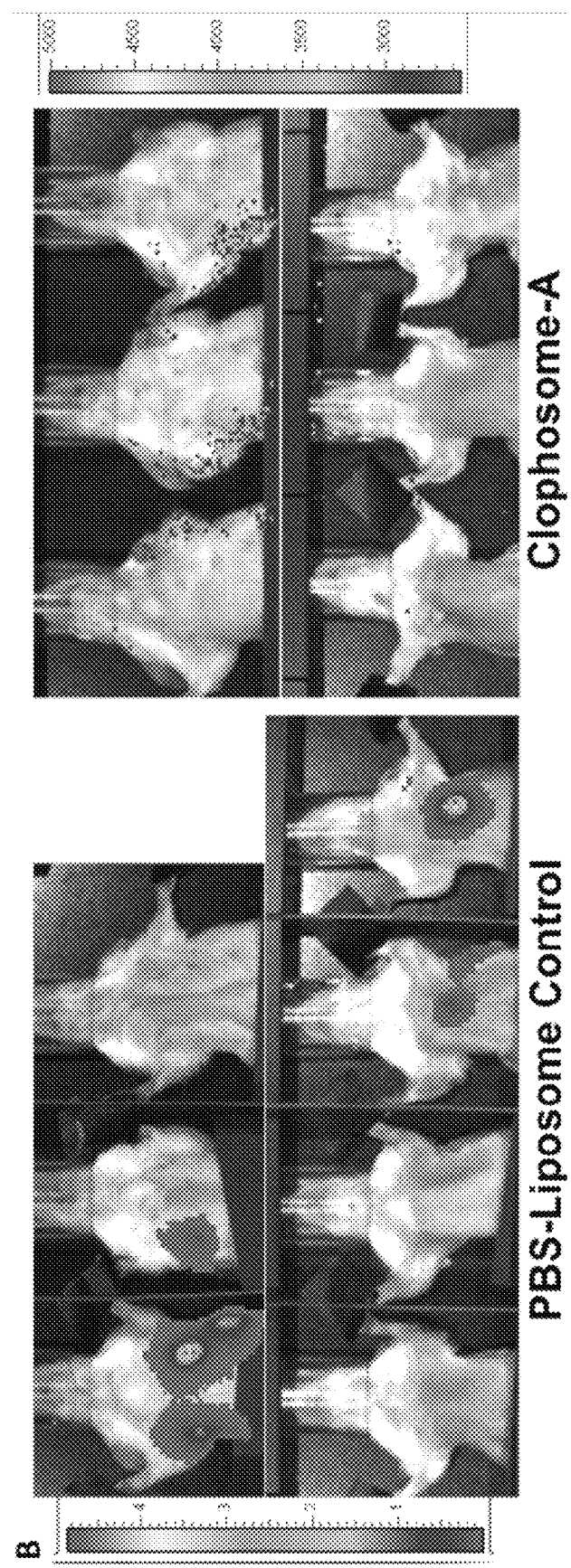
Figure 5C:
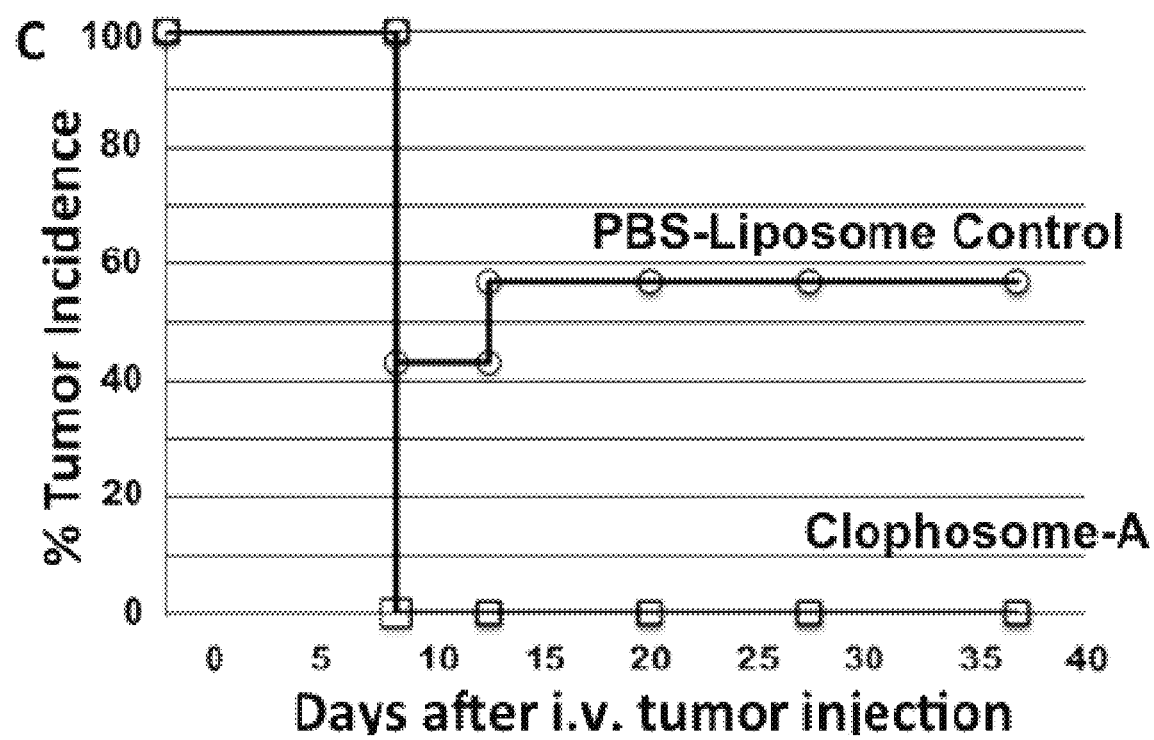
Figure 6A:
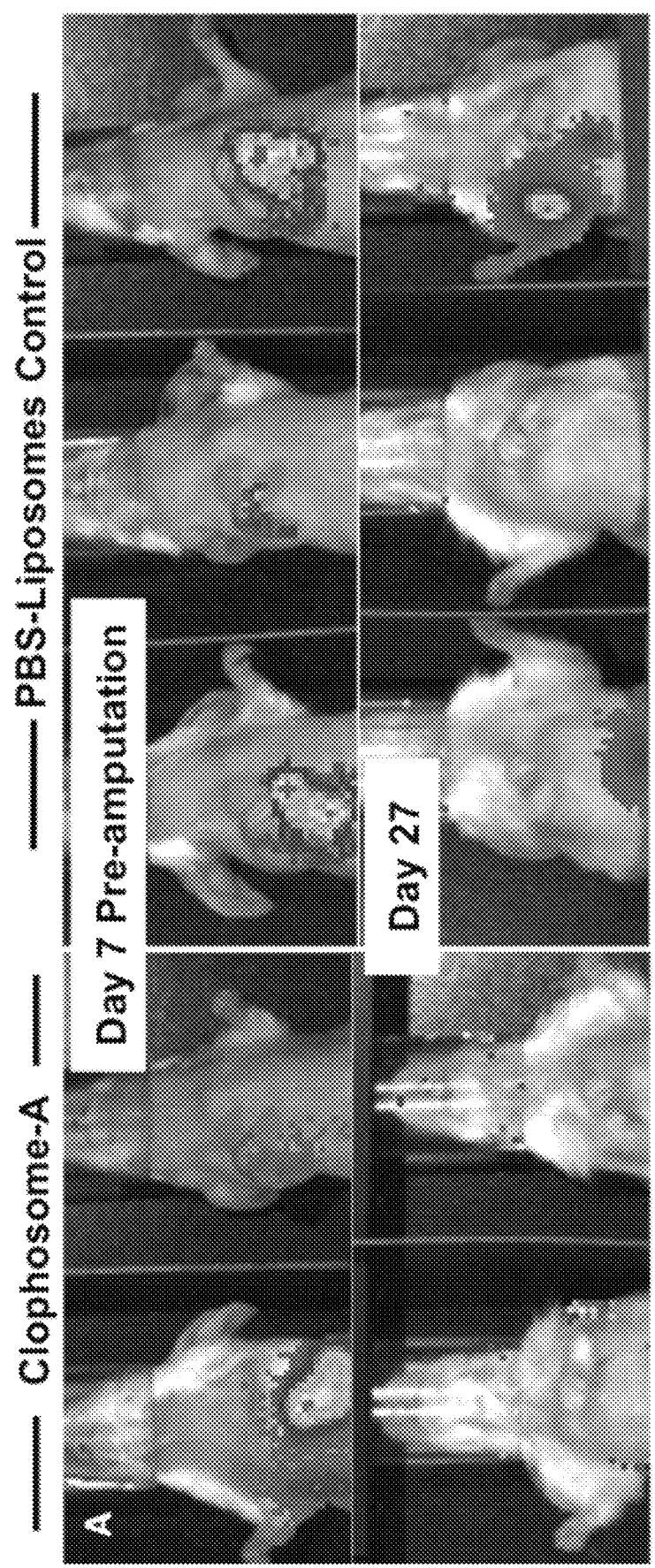
FIGS. 6A-B illustrate depletion of macrohpages after OS metastasis reduces tumor burden. (A) $5\times10^5$ Luc-K7M2 were injected i.t. in proximal right tibia on day 0. On day 7 when pulmonary metastasis were detectable by bioluminescence (top row), mice underwent amputation and 1 dose of intransal clophosome-A (left) or control liposome (right). Lung imaging on day 27 (bottom row) shows absence of lung mets in Clophosome-A group. (B) Overall tumor incidence showing a complete absense of K7M2 pulmonary metastasis in Clophosome-A treated group. (open squares) compared to 50% in the control group (open circles).
Figure 6B:
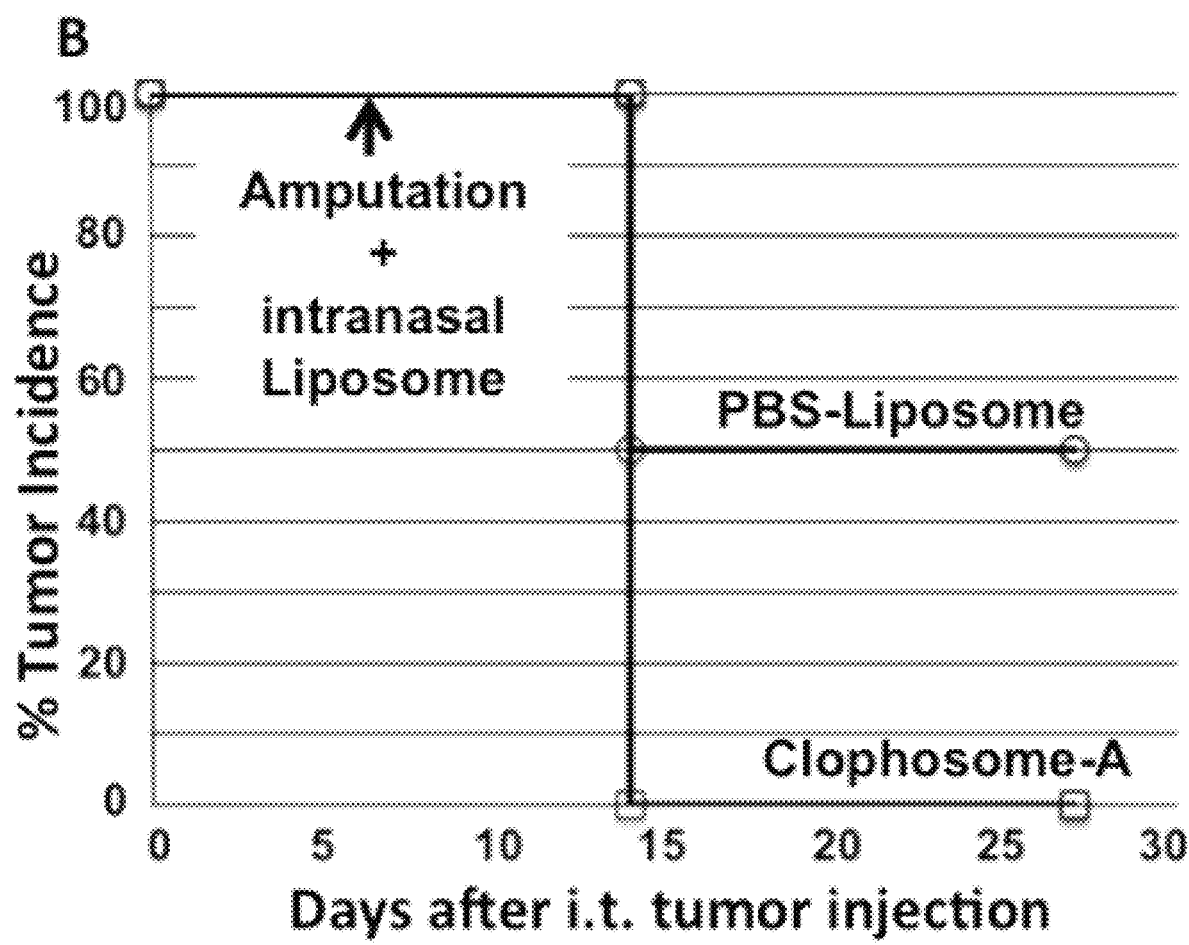

Proliferation was similar in all cells in vitro, ensuring that shRNA transduction did not result in mitogenic effects (data not shown). To follow lung metastasis by bioluminescence, we further introduced luciferase (Luc2) into K7, K7M2, and various K7M2 shRNA cell lines (VCAM-1NS, VCAM-1kd) (FIGS. 4-6). Injection of 1×10$^6$ Luc-K7M2 i.v. resulted in 100% pulmonary disease incidence in 3-4 weeks as evidence by bioluminescence imaging (BLI; FIG. 4A). To confirm disease burden, we performed quantitative RT-PCR (qPT-PCR) of the lung tissues using probes against MuLV envelope gp70 (AH1) transcript, a tumor-associated marker of disease (FIG. 4B). Interestingly, VCAM-1kd K7M2 cells were unable to develop in the lungs when inoculated i.v., suggesting a direct association between VCAM-1 expression on K7M2 and its metastatic potential to the lung (FIG. 4C). Injection at doses of 2.5-5×10⁵ K7M2 i.v. resulted in 60-100% of pulmonary disease in 37-45 days (FIGS. 5B, 5C). Similarly, intratibial (i.t.) injection of 5×10⁵ K7M2 cells followed by leg amputation on day 7 resulted in 50-100% pulmonary disease by day 27 (FIG. 6). Similar pulmonary disease incidence was observed in both Balb/c and athymic nude mice recipients, suggesting that this VCAM-1 mediated differential in vivo growth pattern of K7M2 was a thymic-independent process. As controls, injections of K7 i.v. or i.t. resulted in <20% tumor incidence by day 37, similar to that of VCAM-1kd K7M2 (data not shown).

Figure 7A:
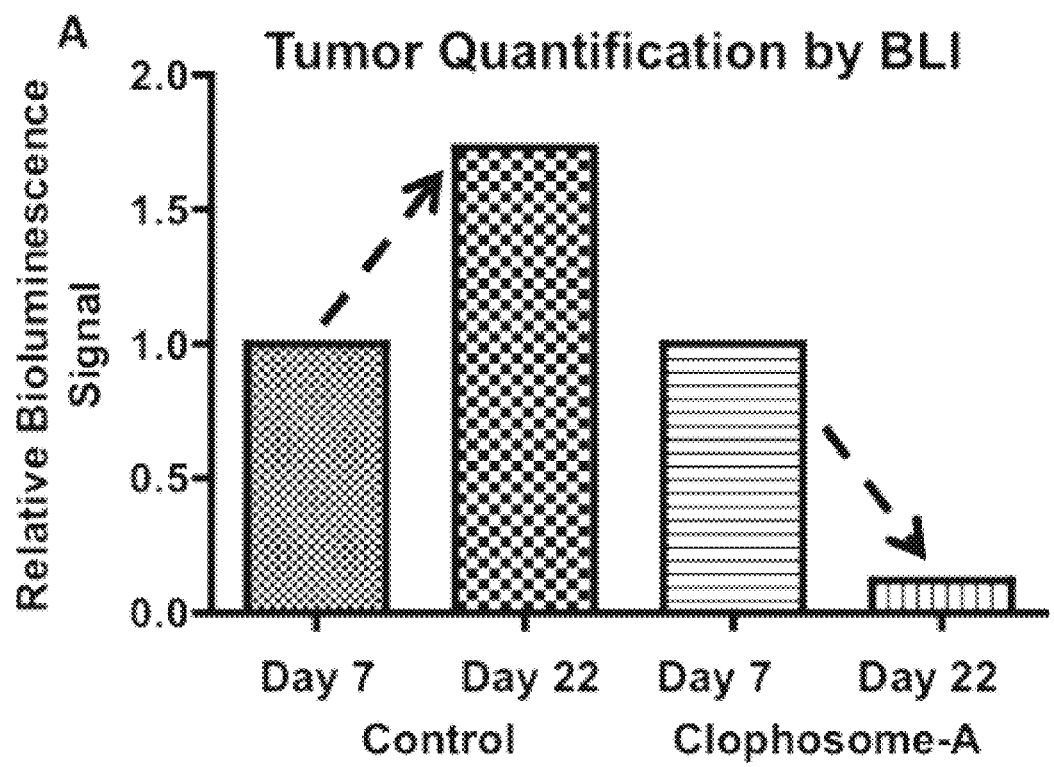
FIGS. 7A-B illustrate clophosome-A depletion of lung macrophages led to disappearance of metastatic OS in the lungs. $5\times10^5$ LUC-K7M2 were injected intratibially into Balb/C mice. The affected leg was then amputated on day 7 when there was evidence of tumor metastatsis in the lungs (A). The mice were then subjected to an intranasal dose of Clophosome-A or PBS-liposome control (Control). The mice were then imaged by bioluminescence for tumor burden (A,B).
Figure 7B:
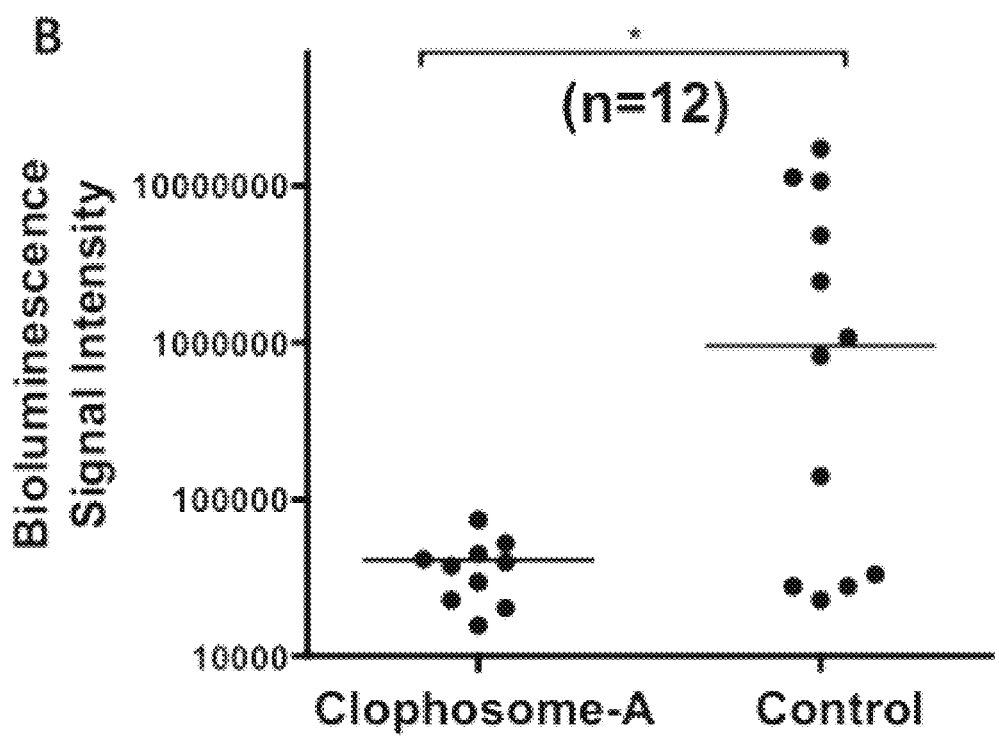

To interrogate whether pulmonary MACs are required for K7M2 metastasis, we depleted MACs by intranasal (i.n.) administration of 50 μl/250 μg liposomal clodronate formulation (Clophosome-A; 5 mg/ml; FormuMax Scientific, Inc.). This procedure depleted pulmonary MACs within 48 hours (FIG. 5A). Strikingly, none of the MACs-depleted animals at the time of K7M2 i.v. challenge developed pulmonary disease (FIGS. 5B, 5C). Clophosome-A administration remained effective when given as late as 7 days after i.t. primary K7M2 tumor inoculation (day 0) and leg amputation procedure (day 7), at a time when pulmonary metastasis was clearly evident by BLI. These animals exhibited 100% disease-free survival by day 22 (FIG. 6). The dramatic reduction of pulmonary disease burden following single i.n. dose of Clophosome-A administration is further revealed by BLI signal intensity (FIG. 7). These data support the rationale to target tumor-associated VCAM-1/α4β1 and pulmonary MACs in preventing or ameliorating pOS.

Figure 8A:
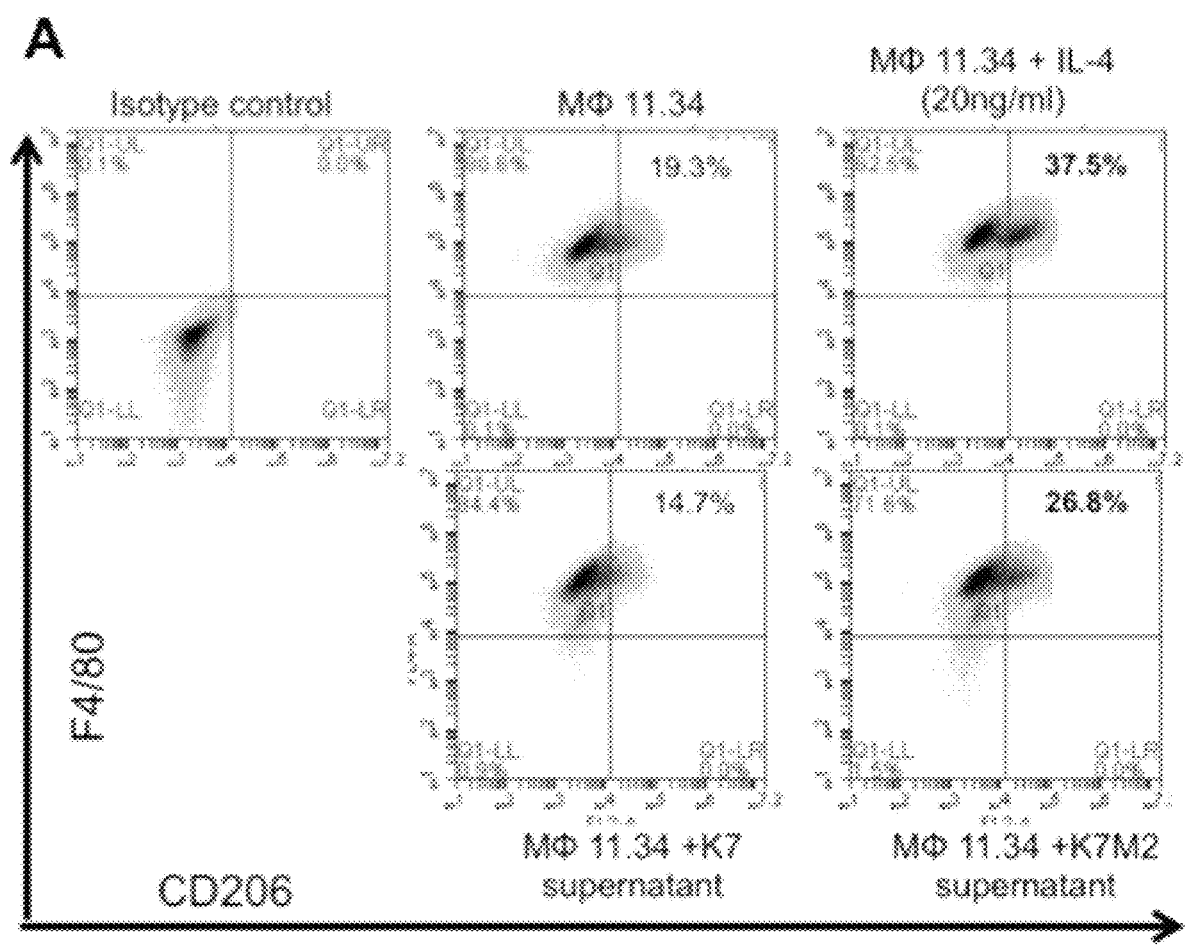
FIGS. 8A-B illustrate K7M2 preferentially induces M2 MACs. (A) MACs line 11.34 were incubated in vitro with OS supernatants from K7 or K7M2 (bottom row) for 48 hours, and the level of CD206 was assessed by flow cytometry. Recombinant IL-4 was used as a positive control for CD206 induction (upper panel). (B) whole-lung extract infused with K7 or K7M2 (upper panel), and VCAM-1kd or control tumor construct (bottom panel) were evaluated for Arg-1 level by qRT-PCR 7 days after tumor inoculation. Normal, uninjected lungs were used as control. *, p<0.05. NS, p>0.05.
Figure 8B:
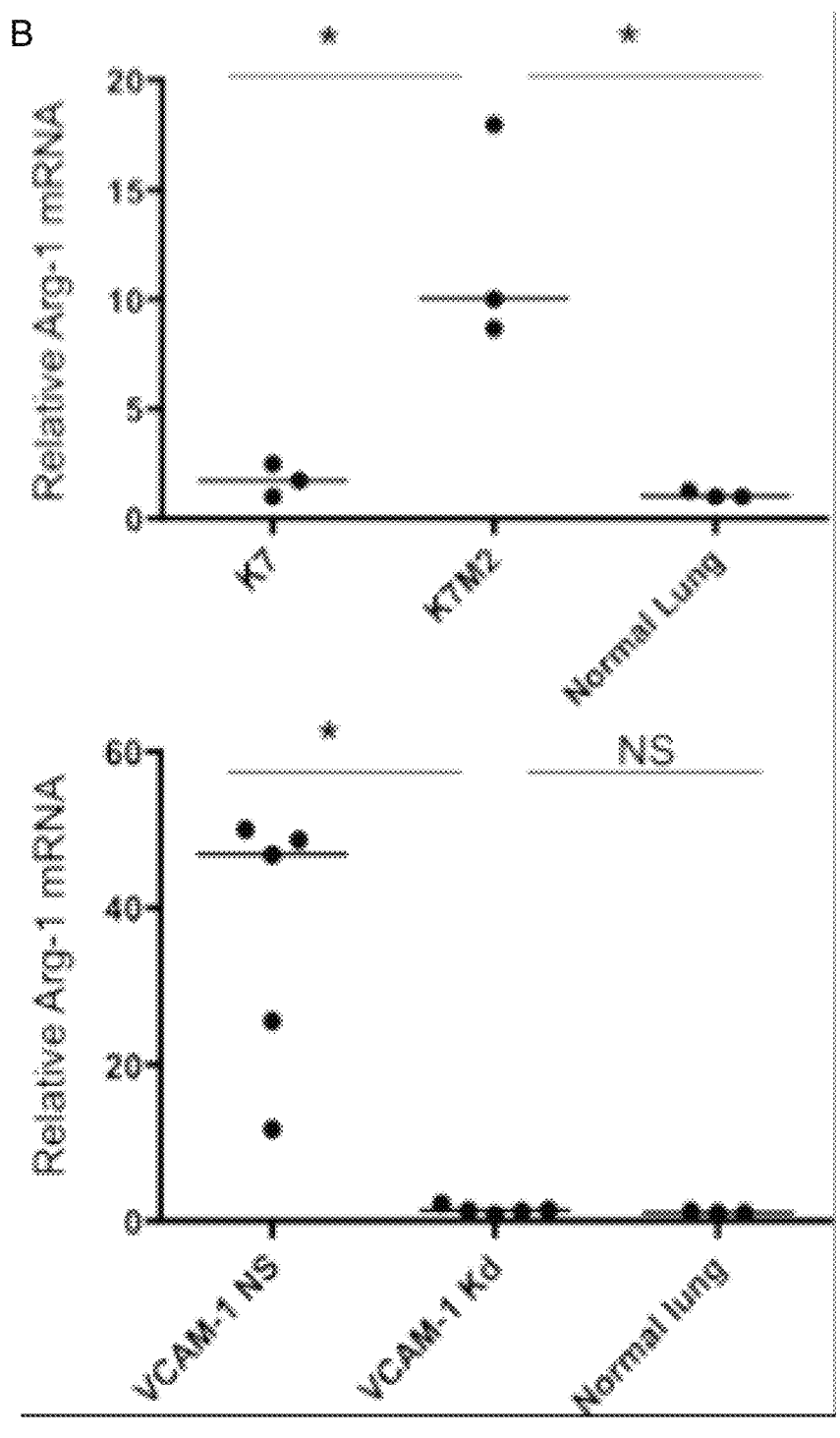

To investigate mechanisms by which tVCAM-1 coax pulmonary MACs into providing a tumor-supportive niche, we tested the ability of K7 and K7M2 supernatants to polarize M0 MACs into either M1 or M2 phenotype. Interestingly, K7M2 supernatant was able to preferentially induce M2 MACs in vitro (as assessed by CD206 expression (FIG. 8A) and Arg-1 production (data not shown)). Corroborating this finding, qRT-PCT of whole-lung extracts revealed that mice injected with K7 or VCAM-1kd K7M2 have similar levels of Arg-1 as the control lung, while the lung tissues injected with VCAM-1$^{hi}$K7M2 displayed elevated levels of Arg-1, consistent with a pro-tumorigenic M2 phenotype (FIG. 8B). We were able to detect sVCAM-1 in the K7M2 spent media by ELISA, while VCAM-1kd K7M2 and K7 WT spent media had reduced to absent sVCAM-1 (data not shown), indicating that K7M2 can influence Mac phentoype either by direct cell-cell contact, or via sVCAM-1 that is shed in the tumor milieu. In addition, sVCAM-1 can be detected in mice harboring K7M2 tumor, raising the interesting prospect that sVCAM-1 could serve as a potential pOS biomarker (data not shown).

Figure 9A:
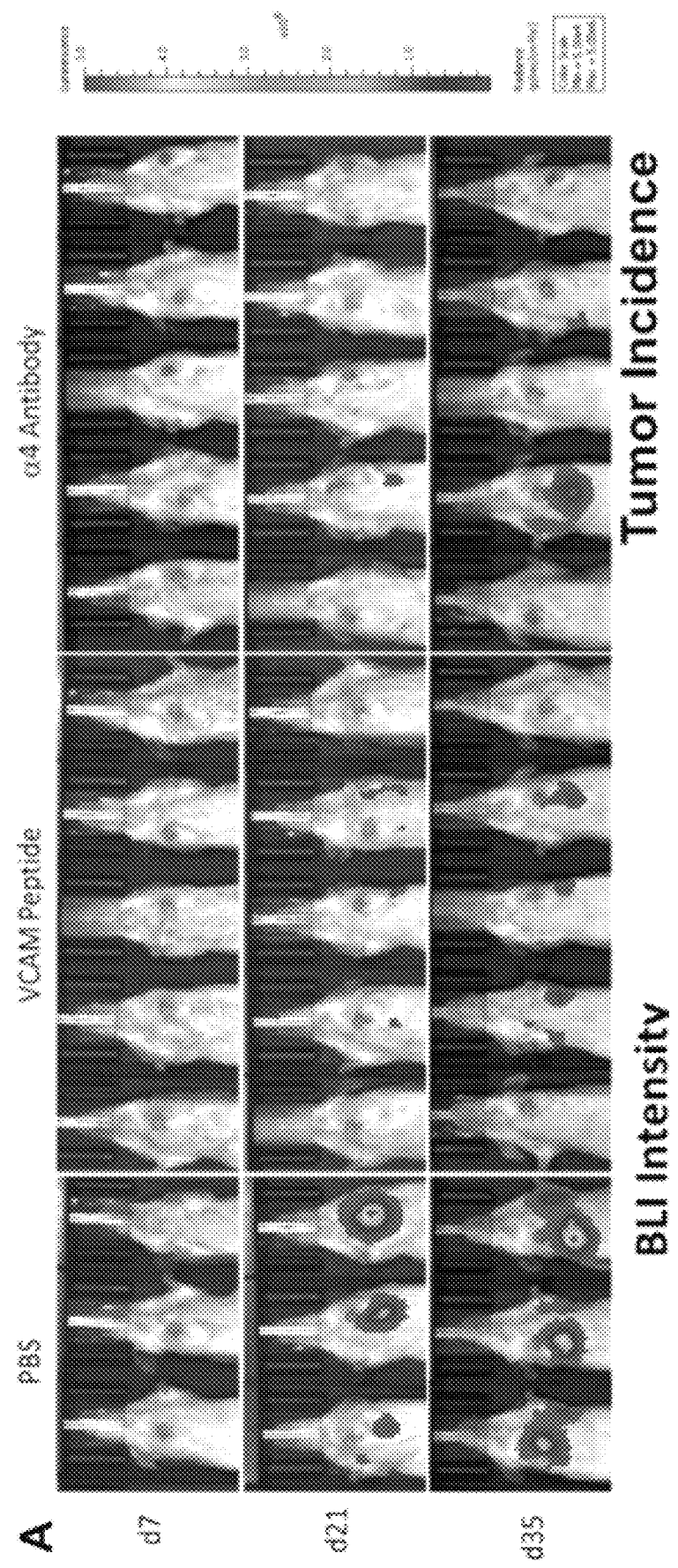
FIGS. 9A-C illustrate targeting site-specific VCAM-1/α4 interaction blunted established pOS growth in vivo. (A) Balb/c mice were inoculated with $5 \times 10^5$ K7M2-luc2 i.v. on Day 0, and then treated with i.n. PBS, 50 µg iVCAM-1p, or 50 µg PS/2 (anti-a4) antibody weekly starting on Day 7. (A) representative images of mice up to 35 days. (B) Relative BLI intensity (Day 7 BLI set as 1) showing reduced tumor burden in pOS animals rescued with i.n. PS/2 antibody (filled circle) or iVCAM-1p (filled triangle) compared to isotype controls (open circle) or control peptide (open triangle). (C) 60% and 80% of pOS mice remained tumor free 1 month after weekly i.n. treatment with PS/2 antibody (filled circle) or iVCAM-1p (filled triangle), respectively. N=5-8 in each cohort.
Figure 9B:
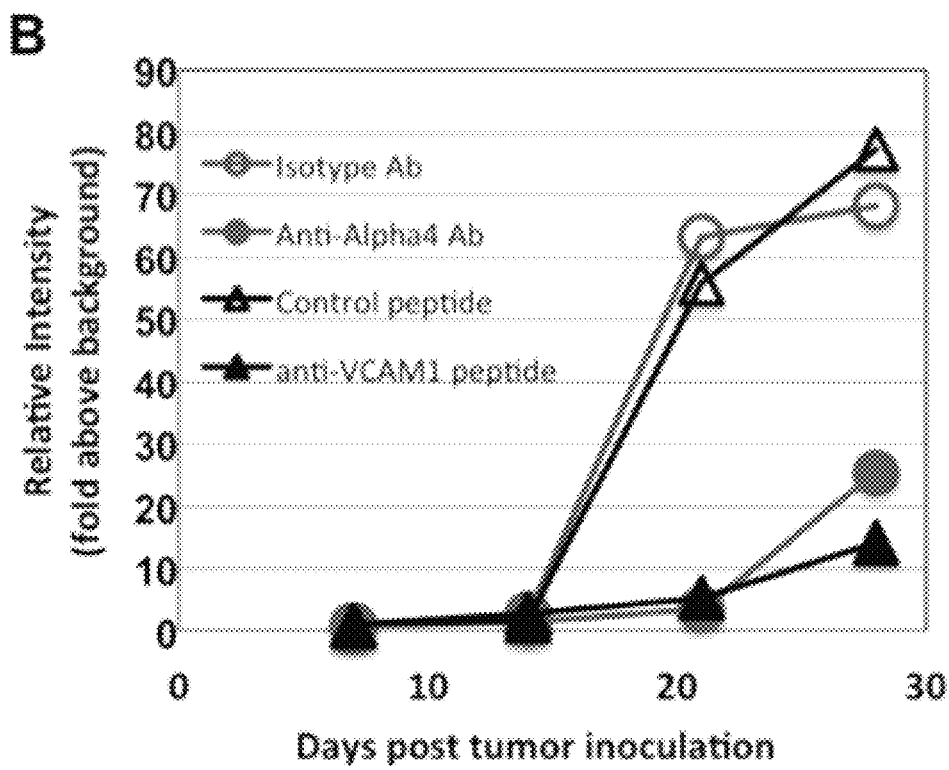
Figure 9C:
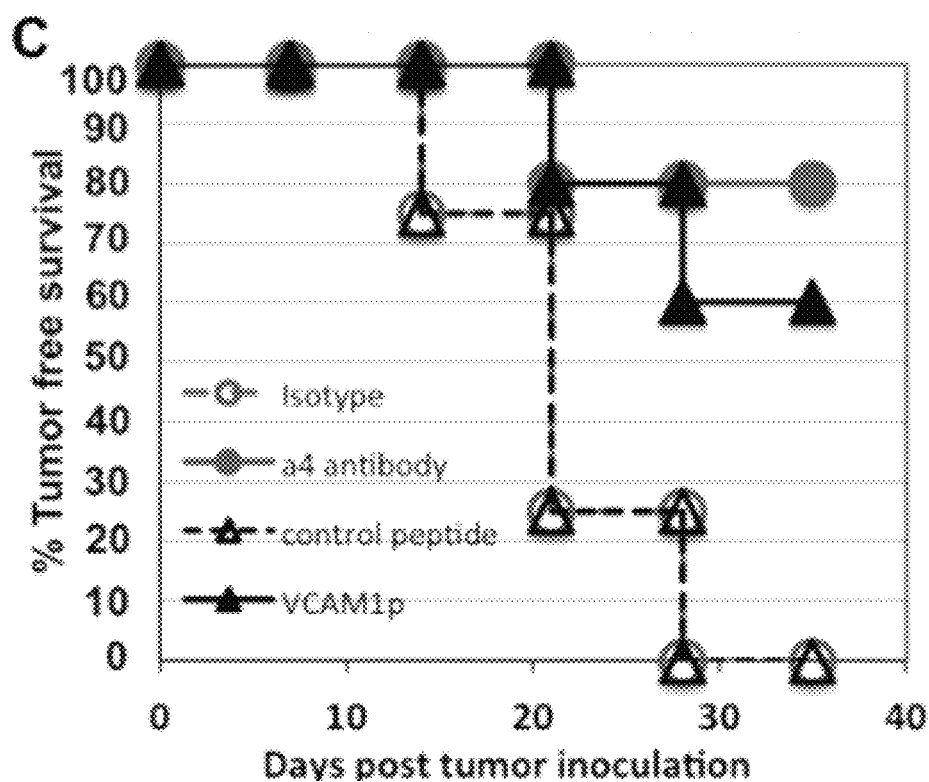
Figure 10:
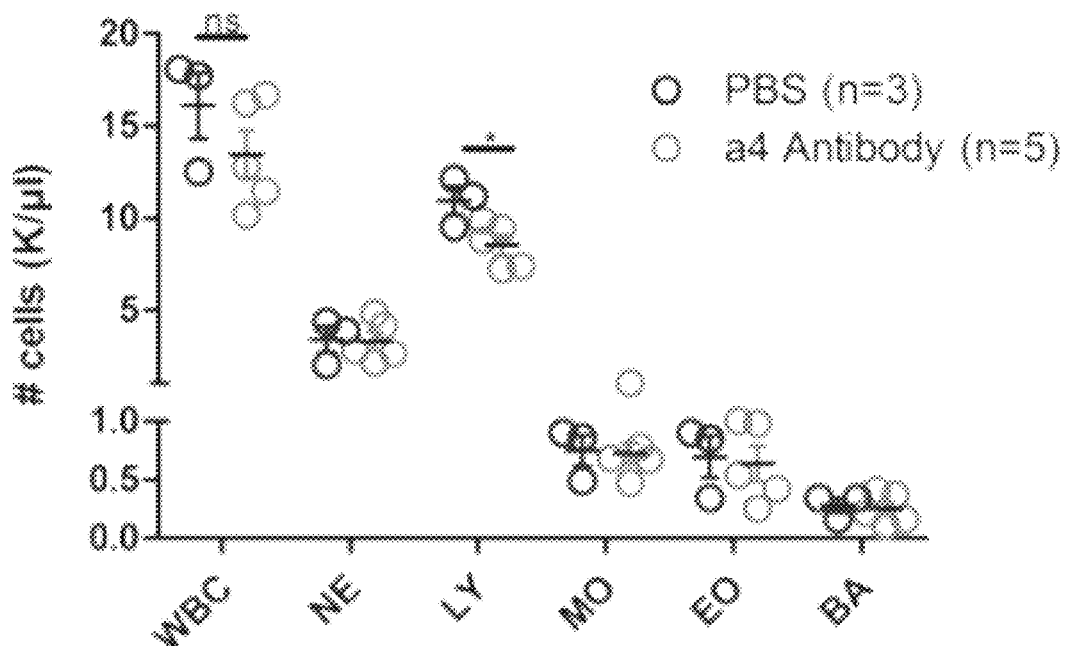
FIG. 10 illustrates PS/2 administration has minimal effect on circulating immune cells. Balb/c mice were treated with 3 consecutive weekly doses of PS/2 antibody (50 µg) dose; red) i.n. and peripheral blood samples were enumerated for immune subtypes. PBS was used as controls. There was statically significant (p=0.045) but small drop in total lymphocyte count in PS/2 group.

To strengthen the crucial link between tVCAM-1 and α4β1 (FIGS. 5-8) and pOS survival, we performed pilot experiments to test whether direct functional blockade of VCAM-1/α4β1 interaction in the lung would result in the same pOS outcome as observed with MACs depletion. In collaboration with Nicole Steinmetz in CWRU School of Engineering, we treated mice (inoculated 7 days prior with a lethal dose of K7M2 i.v.) with weekly i.n. administration of 50 μg of a VCAM-1 inhibitory peptide (iVCAM-1p; amino acid sequence: VHPKQHR (SEQ ID NO: 1)). Weekly i.n. administration of iVCAM-1p starting on Day 7 resulted in a dramatic decreased in pOS tumor burden and incidence (FIG. 9; black triangles). Similarly, weekly administration of 50 ug of anti-α4 mAb (PS/2 clone, ATCC #CRL-1911) i.n. starting on Day 7 post tumor i.v. inoculation resulted in 80% tumor-free rescue and reduced tumor burden among mice with BLI⁺ pOS (FIG. 9; red circles). These pilot observations strengthen our hypothesis that pOS-MAC critically interact through the VCAM-1/α4 axis. As anti-α4 mAb (Natalizumab (Tysabri); Biogen Idec) is already approved by the FDA for treating T-cell mediated autoimmune disorders such as Multiple Sclerosis and Inflammatory Bowel Disease, our finding presents an opportunity to use the same drug for cancer indication with a different route of administration, a potential application that can be tested quickly with pre-clinical demonstration of feasibility, efficacy and toxicity profile prior to IND filing. As we administered mAb via i.n. route, much of the reported side effects of chronic systemic Natalizumab exposure (such as hepatic injury and progressive multifocal leukoencephalopathy) can potentially be limited by reducing the dose and targeting locally in the lung. Examinations of the peripheral blood after 3 weekly doses of PS/2 did not reveal major hematologic toxicity, saved for a small reduction in peripheral lymphocyte count (FIG. 10).

Experimental Design and Research Methods

Functional Outcome of Disrupting MAC-Dependent Survival in pOS

We will use luciferase⁺ VCAM-1$^{lo}$ K7M2 to study metastasis in vivo as compared to VCAM-1NS (VCAM-1$^{hi}$K7M2) and K7. We will also over-express VCAM-1 in K7 and VCAM-1$^{lo}$ K7M2 cells to restore metastatic potential. To address potential off-target effects of shRNA approach, we will also use CRISPR-Cas9 system to silence VCAM-1 gene transcript, a methodology we have employed previously with success. Parallel cell lines will also be created to express luciferase enzyme (Luc-OS) for in vivo tracking by BLI. Each cell lines will be analyzed using qRT-PCR, Western blot, FACS and IHC staining. In vivo behavior will be tested by injecting tumor cells into Balb/c or nude mice (either i.t. followed by amputation on day 7, or directly i.v.) to create lung metastasis (FIGS. 5-6), tracked by BLI twice weekly, and confirmed by gp70 qPCR and IHC of the lungs at the end of the experiments. VCAM-1kd, VCAM-1NS and K7M2 cells will be injected at doses of 2.5-1×10⁶ i.t. or i.v. A parallel set of experiments will be performed with animals treated with 250 μg/50 μl liposomal clodronate i.n. either on Day 0 or on Day 7 following amputation (FIGS. 5 and 6). Tumor-bearing mice will be monitored for dyspnea or cachexia. We will enumerate metastasis by BLI intensity and confirm by tissue necropsy. 10 mice/tumor cell line/group will be tested to derive statistical power. The lung tissues of a parallel cohort treated with liposomal clodronate will be analyzed on days 7, 14, 21 and 28 for the following: 1) We will obtain mRNA to determine presence of VCAM-1, α4β1, AH-1, Arg-1, iNOS, CCL2-CCL5, CXCL9/10, TGF-γ, IL-6, and IL-10; 2) We will examine cellular composition with FACS for CD3, CD8, CD4, CD19, B220, FoxP3, IL-17A, CD11c, CD11b, MHCII, CD40, Ly6C, Ly6G, GR1, F4/80, CD80, CD86 and PD-L1; 3) We will use H&E, IHC and Laser Capture Microdissection (LCM) to evaluate MACs markers including F4/80, CD11b, CD11c, Ly6C, Ly6G, Gr1, iNOS, CD206, and VCAM-1. As more than 80% of human OS over-express VCAM-1 (FIG. 1), we believe that VCAM-1 will play a similarly critical function for human OS. To test VCAM-1 relevance in human and mouse OS beyond K7/K7M2, we will compare VCAM-1 expressions in paired parental: metastatic OS (SAOS-2:LM7; TE85:143B; HuO9: M112; MG63:MG63.3; available in the Huang/Petrosiute Labs), and syngeneic metastatic (RF379L, CR175L, RF229, RF1044, RF892, FC456 and FC456L) and non-metastatic (C2984, RF575, RF1026, RF43) OS lines derived in p53⁺/R172H mouse models (C57BL/6 background; J. Yustein; Texas Children's Hospital). We will also test OS PDXs obtained from patients from the Angie Fowler AYA Cancer Institute (KKOS; Huang) and Texas Children's Hospital (1066, 3441; J. Yustein). We will evaluate OS metastasis in NSG and nude mice or organotypic NSG lung slice cultures that have been depleted of MACs by liposomal clodronate or treating CD11b-DTR mice with diphtheria toxin prior to harvesting lungs. We will manipulate VCAM-1 levels in human and mouse OS with shRNA or CRISPR-Cas9 as discussed.

Figure 12E:
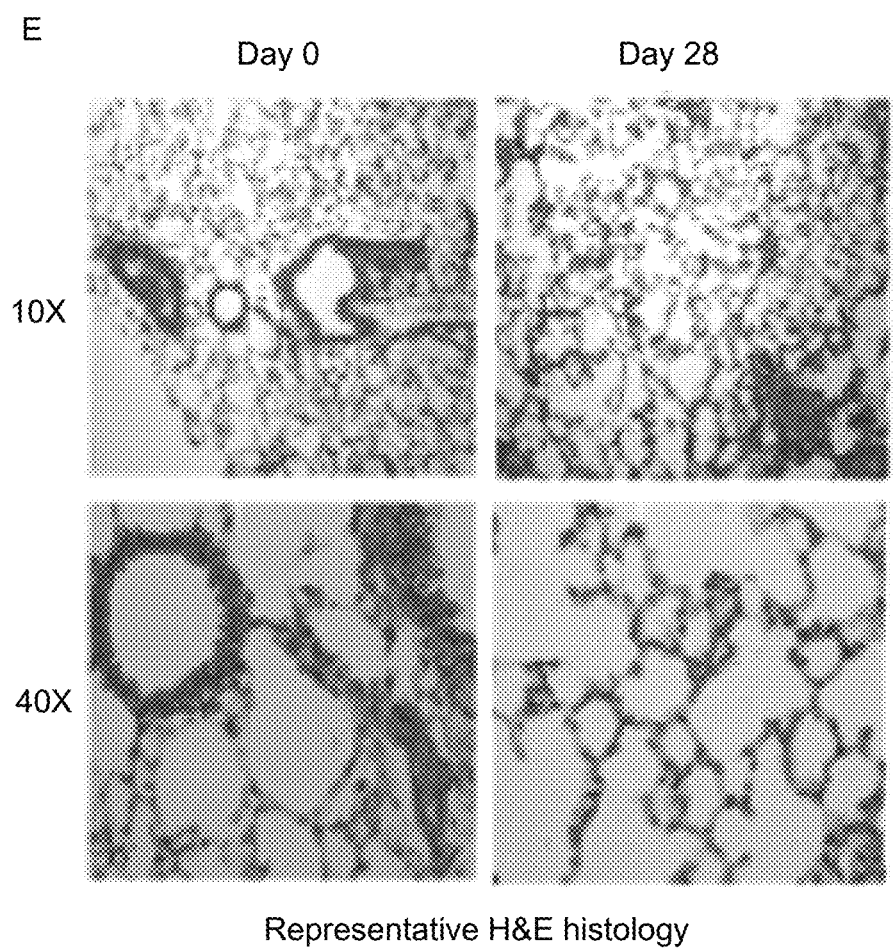

To further understand how ectopic tVCAM-1 promotes metastasis, we will image OS-MAC interactions directly intravitally in the lung. We have also developed long-term lung tissue culture technique in which fluorescent OS growth can be observed in MACs-depleted lung slices cultured at the air-fluid interface over a 3-week period (FIG. 12). Therefore, we possess tools to evaluate individual tumor behavior within intact lung architecture, a significant advancement over current available methods. Our goal is to characterize MACs-dependent responses by measuring the interaction with K7M2 with or without depleting MACs (i.n. liposomal clodronate (FIGS. 5-6) or diphtheria toxin-mediated deletion as in Specific Aim 1.1. We expect that VCAM-$1^{lo}$ tumors will fail to recruit MACs in the tumor niche. We will i.v. inject $2.5\times10^5$-$1\times10^6$ K7M2 (GFP$^+$) with variable VCAM-1 i.v. into NK1.1-depleted CD11b-CFP-F1 (CD11b-CFP (H-$2^b$)×Balb/c (H-$2^d$)) recipient mice. Alternatively, GFP$^+$ RF379L, CR175L and non-metastatic C57BL/6-derived OS lines will be injected into CD11b-CFP-DTR mice with or without diphtheria treatment, or into mice treated with i.n. liposomal clodronate. To discern which subset of MACS preferentially interacts of pOS, we will use CX3CR1$^{+/GFP}$×CCR2$^{+/RFP}$ or CX3CR1$^{GFP/GFP}$×CCR2$^{GFP/GFP}$ (deficient in functional CX3CR1 and CCR2) mice as recipients. At various time points (3, 7, 10, 14 and 21 days), dynamic 3D (750×750×150 um) lung images will be repeated at 30-60 second intervals to yield 4D (xyzt) datasets for analysis. Additionally, we will employ organotypic lung culture approach to supplement the 2P-LSM techniques (FIG. 12).

We expect that interfering tVCAM-1 interaction with MAC α4β1 by depleting MACs or diminishing tVCAM-1 expression will result in regression of established pOS in both mouse and human cell lines in vivo. We also expect to see close association between OS and MAC in the lung parenchyma by imaging, and that depleting MACs will result in pOS establishment failure in tVCAM-1$^+$ OS cell lines and PDXs.

As sVCAM-1 shed by pOS can directly modulate the biology of MACS even without directly cell-to-cell contact (FIG. 8A), we may not observe physical proximity between pOS and MACs in all cases. We will focus on comparing behavior and positional differences of VCAM-1$^{hi}$ and VCAM-1$^{lo}$ OS in the presence or absence of MACs. Our data suggest VCAM-1/α4β1 are critical for pOS survival.

Functional Blockade of VCAM-1/α4β1 on the Outcome of pOS

To test whether pOS-MAC interaction is mediated specifically by VCAM-1/α4β1, we plan to perform a parallel set of experiments using iVCAM-1p or anti-α4 mAb, PS/2, (FIG. 9) in the setting of various human and mouse pOS cells and PDXs. $2.5\times10^5$-$1\times10^6$ luc-pOS cells will be inoculated i.v. into syngeneic mouse (Balb/c or C57BL/6) for mouse pOS and NSG and nude mice for human pOS. Varying doses and frequency of iVCAM-1p, anti-α4 mAb, or both will be administered i.n. starting on day 7 to test for their efficacy in reducing pOS disease burden as measured by BLI. Alternatively, luc-pOS cells will be injected into distal tibia on day 0, and iVCAM-1, anti-α4 mAb, or both will be administered i.n. on Day 7 following leg amputation (FIG. 6). We will use 10 mice per cohort to derive statistical significance. Scrambled peptides or isotype control Ab will be used as controls for iVCAM-1p and anti-α4 mAb treatment, respectively. We are especially interested in a detailed characterization of the cellular infiltration, mRNA expression pattern, and lung architecture in mice treated with varying amount (1 μg, 3 μg, 10 μg, 50 μg, 100 μg, 200 μg) and frequency (weekly, bi-weekly, monthly) of anti-α4 mAb. Since anti-human α4 mAb, Natalizumab (Tysabri) is FDA-approved for autoimmune disease indications, we would like to obtain pre-clinical, IND-enabling data for monitoring systemic and local toxicities and refining optimal dosing regimen. To achieve this, we will document changes in peripheral blood cell counts serially with different dosing schedules of anti-α4 mAb as we have shown in FIG. 10. Mouse serum will be harvested and stored at various time points and assayed for presence of inflammatory chemokines (e.g., TNFγ, IFNγ), and liver and kidney enzyme levels, sVCAM-1. Lung tissues will be harvested and examined for tissue integrity and evidence of inflammation, tissue damage or repair. Furthermore, as patients treated with Natalizumab have been reported to develop progressive multifocal leukoencephalopathy, we will harvest mouse brain for IHC examination for any gross abnormalities.

Figure 11:
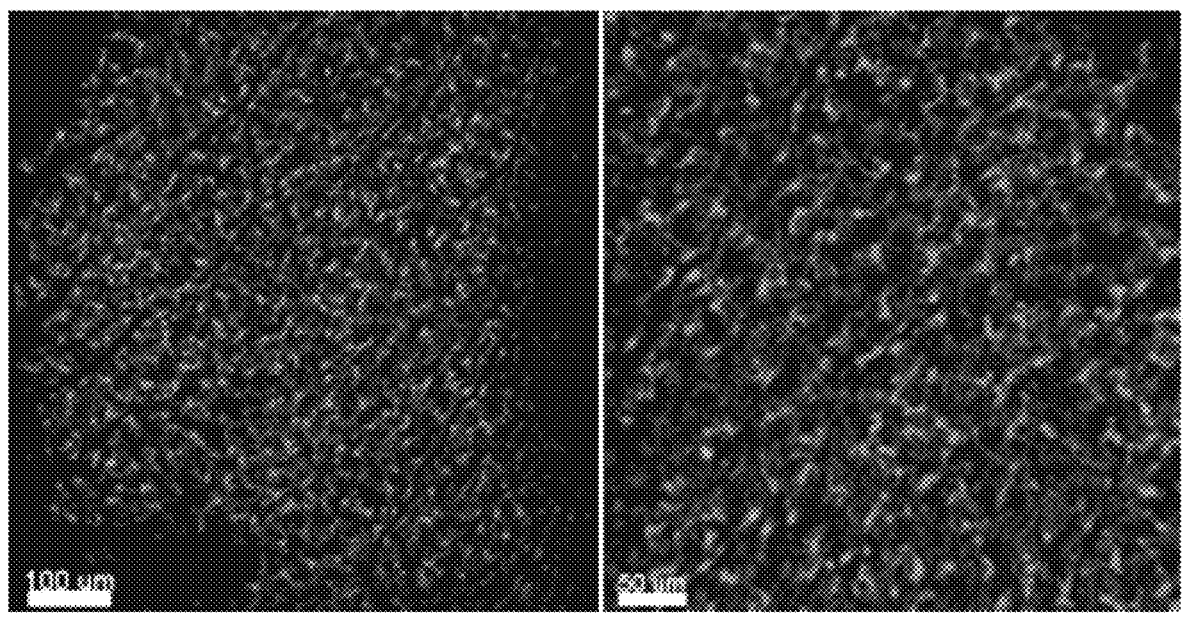
FIG. 11 illustrates Intravital 2P-LSM images of mouse lung. Snapshots of a 2P-LSM lung imaging from a CX3CR1GFP$^{/+}$/CCR2$^{RFP/+}$ double reporter mouse, showing large number of CX3R1$^+$ (Green) and occasional CCR2$^+$ (red) monocyte & macrophage populations in the lung tissue under physiological conditions. The underlying lung tissues can be visualized by second harmonic signal generation under 2P-LSM (blue) due to collagen-rich stromal tissue (Unpublished results).

We will evaluate mouse pOS-MAC interaction in situ using 2P-LSM or organotypic lung slices (FIGS. 11, 12) of green-red fluorescent reporter mice (CX3CR1$^{+/GFP}$×CCR2$^{+/GFP}$; CX3CR1$^{GFP/GFP}$×CCR2$^{GFP/GFP}$) using CFP-pOS (blue), or of CD11b-CFP (blue) reporter mice using GFP-pOS (green). These live, in situ imaging between mouse pOS and MACs will be carried out in the presence or absence of iCAM-1p, PS/2 (anti-α4 mAb) or both.

Results

We expect that interfering tVCAM-1 interaction with α4β1 on MACS using anti-α4 mAb will result in regression of established pulmonary disease in both mouse and human OS cell lines in vivo. We also expect to see close association between OS and MAC in the lung parenchyma via intravital 2P-LSM imaging, and that interfering VCAM-1/α4β1 signaling will interfere with this close physical association.

Our preliminary data strongly suggest VCAM-1/α4β1 are critical for pOS survival, and we have experience with i.n. administration of iVCAM-1p and anti-α4 mAb. Therefore, we do not expect technical difficulties with these approaches. To prolong iVCAM-1p availability, we may develop liposomal formulation for iVCAM-1p, or incorporate peptide on the surface of plant-based nanoparticles.

The impact of tVCAM-1 signaling on pOS will be considered significant if p<0.05 using ANOVA with GraphPad InSTAT Software. We will use 10 mice per tumor condition for all in vivo experiments. At least 5 animals per imaging experiment will be performed. For in vivo experiments, log rank analysis of Kaplan-Meier plot will be performed using MedCalc software. We will consult Dept. of Epidemiology and Biostatistics to obtain power calculations needed to ensure statistically meaningful data acquisition.

From the above description, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of treating pulmonary metastasis of osteosarcoma cells (pOSs) in a subject in need thereof, comprising intranasal or inhalation administering to the subject a therapeutically effective amount of Natalizumab.

2. The method of claim 1, wherein the Natalizumab is administered at an amount sufficient to inhibit pOSs growth, and/or metastases, and/or metastatic spread.

3. The method of claim 1, further comprising treating the subject with a combination cancer therapy, wherein the combination cancer therapy comprises an immunotherapy, a radiation therapy, or a chemotherapy.

4. The method of claim 1, wherein the pOSs overexpress VCAM-1 on the surface of the cells compared to parental tumor cells.

* * * * *